US006822075B2

(12) United States Patent
Björck et al.

(10) Patent No.: US 6,822,075 B2
(45) Date of Patent: Nov. 23, 2004

(54) PROTEIN L AND HYBRID PROTEINS THEREOF

(75) Inventors: Lars Björck, Södra Sandby (SE); Ulf Sjöbring, Lund (SE)

(73) Assignee: Affitech AS, Oslo (NO)

( * ) Notice: Subject to any disclaimer, the term of this patent is extended or adjusted under 35 U.S.C. 154(b) by 0 days.

(21) Appl. No.: 08/325,278

(22) PCT Filed: Apr. 28, 1993

(86) PCT No.: PCT/SE93/00375

§ 371 (c)(1),
(2), (4) Date: Oct. 26, 1994

(87) PCT Pub. No.: WO93/22342

PCT Pub. Date: Nov. 11, 1993

(65) Prior Publication Data

US 2003/0027283 A1 Feb. 6, 2003

(30) Foreign Application Priority Data

Apr. 28, 1992 (SE) .............................................. 9201331

(51) Int. Cl.[7] .......................... A61K 38/00; A61K 39/00; C07K 1/00; C07K 16/00; C07K 17/00
(52) U.S. Cl. ........................ 530/350; 530/402; 530/300; 530/324; 530/388.4; 424/234.1; 424/190.1; 424/197.11; 435/7.1; 435/975
(58) Field of Search ................. 530/350, 300, 530/402, 324, 388.4; 424/234.1, 190.1, 197.11; 435/7.1, 975

(56) References Cited

U.S. PATENT DOCUMENTS

| | | | |
|---|---|---|---|
| 5,108,894 A | * | 4/1992 | Björck et al. |
| 5,180,810 A | * | 1/1993 | Gomi et al. |
| 5,278,297 A | * | 1/1994 | Gomi et al. |
| 5,312,901 A | | 5/1994 | Fahnestock ................. 530/350 |
| 5,840,316 A | * | 11/1998 | Singh et al. |
| 5,858,677 A | * | 1/1999 | Forsgren |
| 5,965,390 A | * | 10/1999 | Bjorck et al. |
| 5,977,336 A | * | 11/1999 | Barenkamp |
| 5,989,828 A | * | 11/1999 | Forsgren |
| 6,162,903 A | * | 12/2000 | Trowern et al. |
| 2002/0137918 A1 | * | 9/2002 | Gore et al. .............. 536/23.53 |
| 2003/0017168 A1 | * | 1/2003 | Wick et al. ............... 424/185.1 |
| 2003/0027283 A1 | * | 2/2003 | Bjorck et al. .............. 435/69.3 |

FOREIGN PATENT DOCUMENTS

| | | |
|---|---|---|
| EP | 0255497 | 2/1988 |
| WO | 8705631 | 9/1987 |
| WO | WO93/22342 | * 11/1993 |
| WO | WO93/22439 | * 11/1993 |

OTHER PUBLICATIONS

Wikstrom et al Eur. J. Biochem. 235:543–548, 1996.*
Kihlberg et al, Eur. J. Biochem. 240:556–563, 1996.*
Svensson et al. Eur. J. Biochem. 258:890–896, 1998.*
Wikström et al, J. Mol. Biol. 250:128–133, 1995.*
Murphy et al DNA Sequence—J. DNA Sequencing and Mapping 4/259–265, 1994.*
Yu et al, Archives of Andrology 32:219–225, 1994.*
Wikström et al, Biochemistry, 33:14011–14017, 1994.*
Axcrona et al, Scand J. Immunol. 42:359–367, 1995.*
deChâteau et al, Scand. J. Immunol 37:399–405, 1993.*
Nilson et al, J. Immunol. Methods 164:33–40, 1993.*
Beckingham et al, Biochem. J. 340:193–199, 1999.*
Enokizono et al, J. Mol. Biol. 270:8–13, 1997.*
Derrick et al Nature 359:752–754, 1992.*
Bjorck. J. Immunology, 140;4:1194–97, 1988.*
Akerström et al, JBC, 264/39:19740–46, 1989.*
Kihlberg et al JBC, 257/35:25583–588, 1992.*
Vola et al, Cell Biophysics 24/25:27–36, 1994.*
Riechmann et al, J. Biomolecular NMR 6:141–152, 1995.*
Burgess et al. J. Cell Biology 111: 2129–38, 1990.*
Cozer et al. Mol. Cell Biology 8637: 1247–52, 3/88.*
Bowie et al Science 247:1306–1310, 3/90.*
Akerstrom and Björck, "Protein L: An Immunoglobulin Light Chain–binding Bacterial Protein," *The Journal of Biological Chemistry* 264(33): 19740–19746, 1989.
Alberts, *Molecular Biology of The Cell*, 2$^{nd}$ ed., Garland Publishing Inc., New York, 1989, p. 265.
Château et al., "On the Interaction between Protein L and Immunoglobulins of Various Mammalian Species," *Scand. J. Immunol.* 37: 399–405, 1993.
Elbashir et al., "Antibody response in immunized rabbits measured with bacterial immunoglobulin–binding proteins," *Journal of Immunological Methods* 135: 171–179, 1990.
The Journal of Biological chemistry, vol. 267, No. 18, 1992, William Kastern et al,pp. 12820–12825 "Structure of peptostreptococcal Protein L and Identification of a Reeated Immunoglobul in Light Chain–binding Domain".
Infection and Immunity, 58 (May 1990) :5 William Kastern et al: "Protein L, a Bacterial Immunoglobulin–Binding Protein and Possible virulence Determinant", p. 1217–p. 1222; see especially fig. 4 and 5.
Kihlberg et al., "Protein LG: A Hybrid Molecule with Unique Immunoglobulin Binding Properties," *The Journal of Biological Chemistry* 267(35): 25583–25588, 1992.

(List continued on next page.)

*Primary Examiner*—N. M. Minnifield
(74) *Attorney, Agent, or Firm*—Kalow & Springut LLP

(57) ABSTRACT

The invention relates to sequences of protein L which bind to light chains of immunoglobulins. The invention also relates to hybrid proteins thereof which are able to bind to both light and heavy chains of immunoglobulin G, in particular protein LG. The invention also relates to DNA-sequences which code for the proteins, vectors which include such DNA-sequences, host cells which have been transformed with the vectors, methods for producing the proteins, reagent appliances for separation and identification of immunoglobulins, compositions and pharmaceutical compositions and pharmaceutical compositions which contain the proteins.

7 Claims, 18 Drawing Sheets

OTHER PUBLICATIONS

Lämmler et al., "Characterization of albumin–binding properties of *Peptostreptococcus magnus*," *Can. J. Microbiol.* 35: 614–618, 1989.

Nilson et al., "Protein L from *Peptostreptococcus magnus* Binds to the k Light Chain Variable Domain," *The Journal of Biological Chemistry* 267(4): 2234–2239, 1992.

Patella et al., "A Bacterial Ig–Binding Protein That Activates Human Basophils and Mast Cells," *The Journal of Immunology* 145(9): 3054–3061, 1990.

* cited by examiner

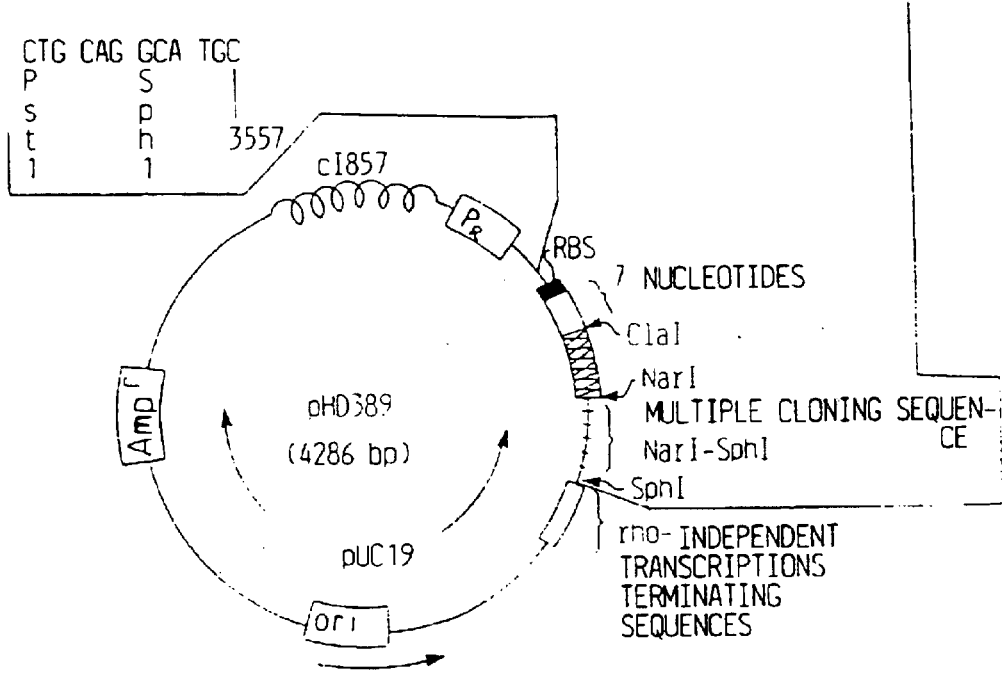
FIG. 1 PLASMA pHD 389. THE RIBOSOMAL BINDING-SEQUENCE (EMPHASIZED WITH A FULL LINE), THE SEQUENCE FOR SIGNAL PEPTIDE FROM ompA (FROM E.coli) (DOTTED LINE) AND RECOGNITION SEQUENCE FOR SEVERAL RESTRICTION ENZYMES ARE SHOWN.

```
                 v                        v                             v
AAACTTGTTATTAATGGTAAAACATTGAAAGGCGAAACAACTACTAAAGCAGTAGACGCA            1200
LysLeuValIleAsnGlyLysThrLeuLysGlyGluThrThrThrLysAlaValAspAla             400 v                       v                          v
GAAACTGCAGAAAAAGCCTTCAAACAATACGCTAACGACAACGGTGTTGATGGTGTTTGG            1260
GluThrAlaGluLysAlaPheLysGlnTyrAlaAsnAspAsnGlyValAspGlyValTrp             420 v                      v
ACTTATGATGATGCCGACTAAGACCTTTACGGTAACTGAAATGTAATAA   -    -              1308
ThrTyrAspAspAlaThrLysThrPheThrValThrGluMet    -    -                     434
```

FIG. 2

PROTEIN LG

```
                    v                    v                    v
GCGGTAGAAAATAAGAAGAAACACCAGAAACTGATTCAGAGAAGAAGTA           60
AlaValGluAsnLysGluThrProGluThrAspSerGluGluGluVal            20
         →B1
          v                    v                    v
ACAATCAAAGCTAACCTAATCTTTGCAAATGGAAGCACACAAACTGCAGAATTCAAAGGA 120
ThrIleLysAlaAsnLeuIlePheAlaAsnGlySerThrGlnThrAlaGluPheLysGly  40 v                    v                    v
ACATTTGAAAAGCAACATCAGAGCTTATGCGTATGCAGATACTTTGAAGAAAGACAAT   180
ThrPheGluLysGlnHisGlnSerLeuCysValCysArgTyrPheGluGluArgGlnAsn 60 v                    v                    v
GGAGAATATACTGTAGATGTTGCAGATAAGGTTATACTTTAAATATTAAATTTGCTGGA  240
GlyGluTyrThrValAspValAlaAspLysValIleLeuAsnIleLysPheAlaGly    80
     →B2
          v                    v                    v
AAAGAAAAAACACCAGAAGAACCAAAGAAGAAGTTACTATTAAAGCAAACTTAATCTAT  300
LysGluLysThrProGluGluProLysGluValThrIleLysAlaAsnLeuIleTyr    100 v                    v                    v
GCAGATGGAAAAACAGCAGAATTCAAAGGAACATTGAAGAAGCAACAGCAGAA        360
AlaAspGlyLysThrAlaGluPheLysGlyThrPheGluGluAlaThrAlaGlu       120
```

FIG. 2
(CONT.)

```
                                                                                v
GCATACAGATATGCAGATGCATTAAAGAAGGACAATGGAGAATATACAGTAGACGTTGCA                    420
AlaTyrArgTyrAlaAspAlaLeuLysLysAspAsnGlyGluTyrThrValAspValAla                    140
                                    ┌─> B3
                v                   v                                           v
GATAAAGGTTATACTTTAAATATTAAATTTGCTGGAAAGAAAAACACCAGAAGAACCA                      480
AspLysGlyTyrThrLeuAsnIleLysPheAlaGlyLysGluLysThrProGluGluPro                    160 v                                   v                           v
AAAGAAGAAGTTACTATTAAAGCAAACTTAATCTATGCAGATGGAAAAACACAAACAGCA                    540
LysGluGluValThrIleLysAlaAsnLeuIleTyrAlaAspGlyLysThrGlnThrAla                    180 v                                   v                           v
GAATTCAAAGGAACATTTGAAGAAGCAACAGCAGAAGCATACAGATATGCTGACTTATTA                    600
GluPheLysGlyThrPheGluGluAlaThrAlaGluAlaTyrArgTyrAlaAspLeuLeu                    200 v                                   v                           v
GCAAAAGAAAATGGTAAATATACAGTAGACGTTGCAGATAAAGGTTATACTTTAAATATT                    660
AlaLysGluAsnGlyLysTyrThrValAspValAlaAspLysGlyTyrThrLeuAsnIle                    220
                            ┌─> B4
                v           v                       v                           v
AAATTTGCTGGAAAGAAAAAACACCAGAAGAACCAAAAGAAGAAGTTACTATTAAAGCA                     720
LysPheAlaGlyLysLysLysThrProGluGluProLysGluGluValThrIleLysAla                    240 v                                   v                           v
AACTTAATCTATGCAGATGGAAAAACTCAAACAGCAGAGTTCAAAGGAACATTTGCAGAA                    780
AsnLeuIleTyrAlaAspGlyLysThrGlnThrAlaGluPheLysGlyThrPheAlaGlu                    260
```

FIG. 2 (CONT.)

```
                                                                          v                      v
GCAACAGCAGAAGCATACAGATACGCTGACTTATTAGCAAAAGAAAATGTAAATATACA              840
AlaThrAlaGluAlaTyrArgTyrAlaAspLeuLeuAlaLysGluAsnGlyLysTyrThr             280
                                                                        B5
        v                    v                      v    ↑      v
GCAGACTTAGAAGATGGTGGATACACTATTAATATTAGATTTGCAGGTAAGAAAGTTGAC             900
AlaAspLeuGluAspGlyGlyTyrThrIleAsnIleArgPheAlaGlyLysLysValAsp             300
                                        C1
       v          v     ↑      v           ↓         v
GAAAAACCAGAAGAACCCATGGACACTTACAAATTAATCCTTAATGGTAAAACATTGAAA             960
GluLysProGluGluProMetAspThrTyrLysLeuIleLeuAsnGlyLysThrLeuLys             320
        v                    v                      v                   v
GGCGAAACAACTACTGAAGCTGTTGATGCTGCTACTGCAGAAAAGTCTTCAAACAATAC              1020
GlyGluThrThrThrGluAlaValAspAlaAlaThrAlaGluLysValPheLysGlnTyr             340
        v                    v                      v                   v
GCTAACGACAACGGTGTTGACGGTGAATGGACTTACGACGATGCGACTAAGACCTTTACA             1080
AlaAsnAspAsnGlyValAspGlyGluTrpThrTyrAspAspAlaThrLysThrPheThr             360
  ↑ D                                                      C2
   v                    v                      v    ↑
GTTACTGAAAAACCAGAAGTGATCGATGCGTCTGAATTAACACCAGCCGTGACAACTTAC             1140
ValThrGluLysProGluValIleAspAlaSerGluLeuThrProAlaValThrThrTyr             380
```

FIG. 2
(CONT.)

FIG. 3 SCHEMATIC OVERALL VIEW OF THE PRODUCTION OF PROTEIN L

FIG. 4 SCHEMATIC OVERALL VIEW OF PRODUCTION OF PROTEIN LG

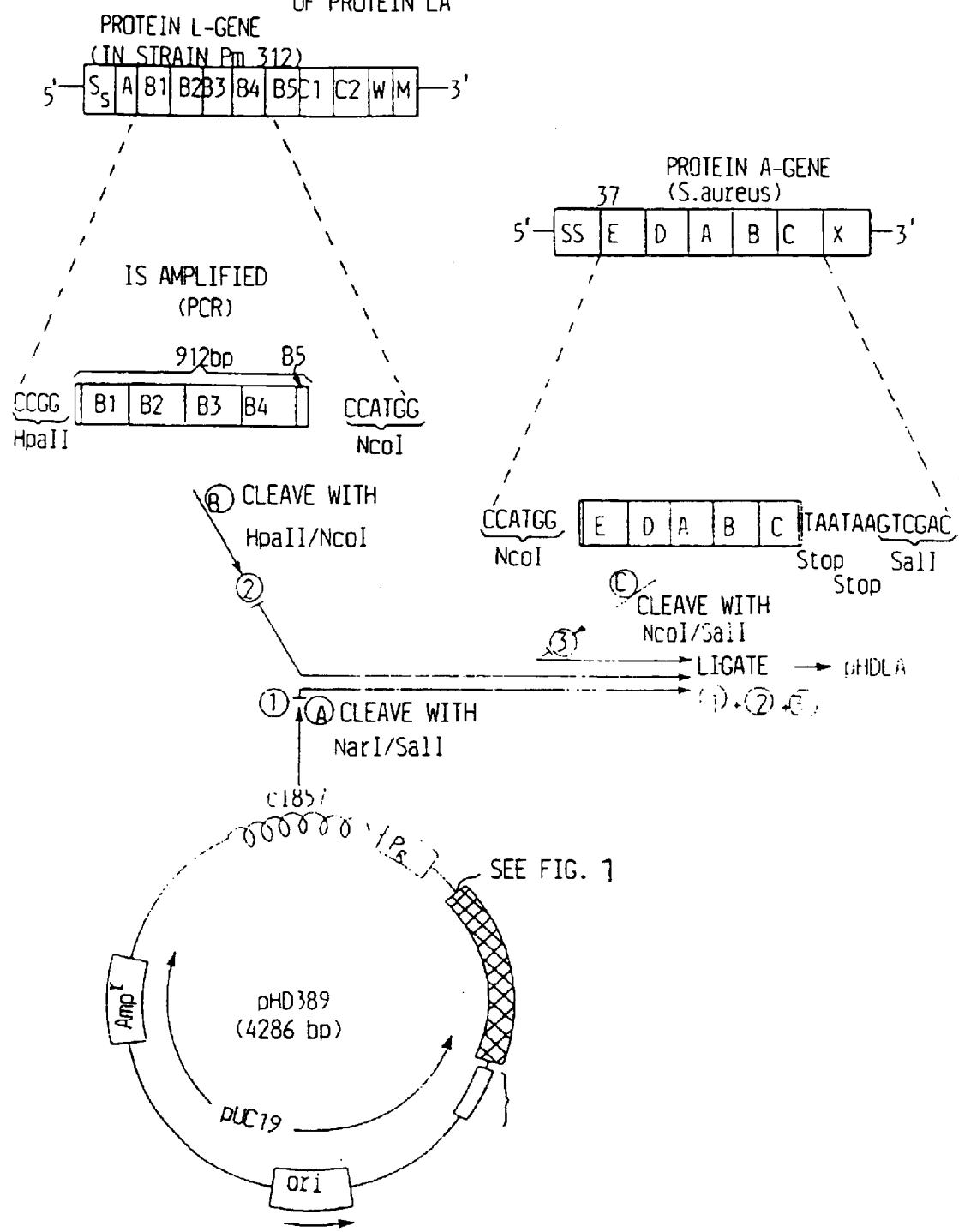

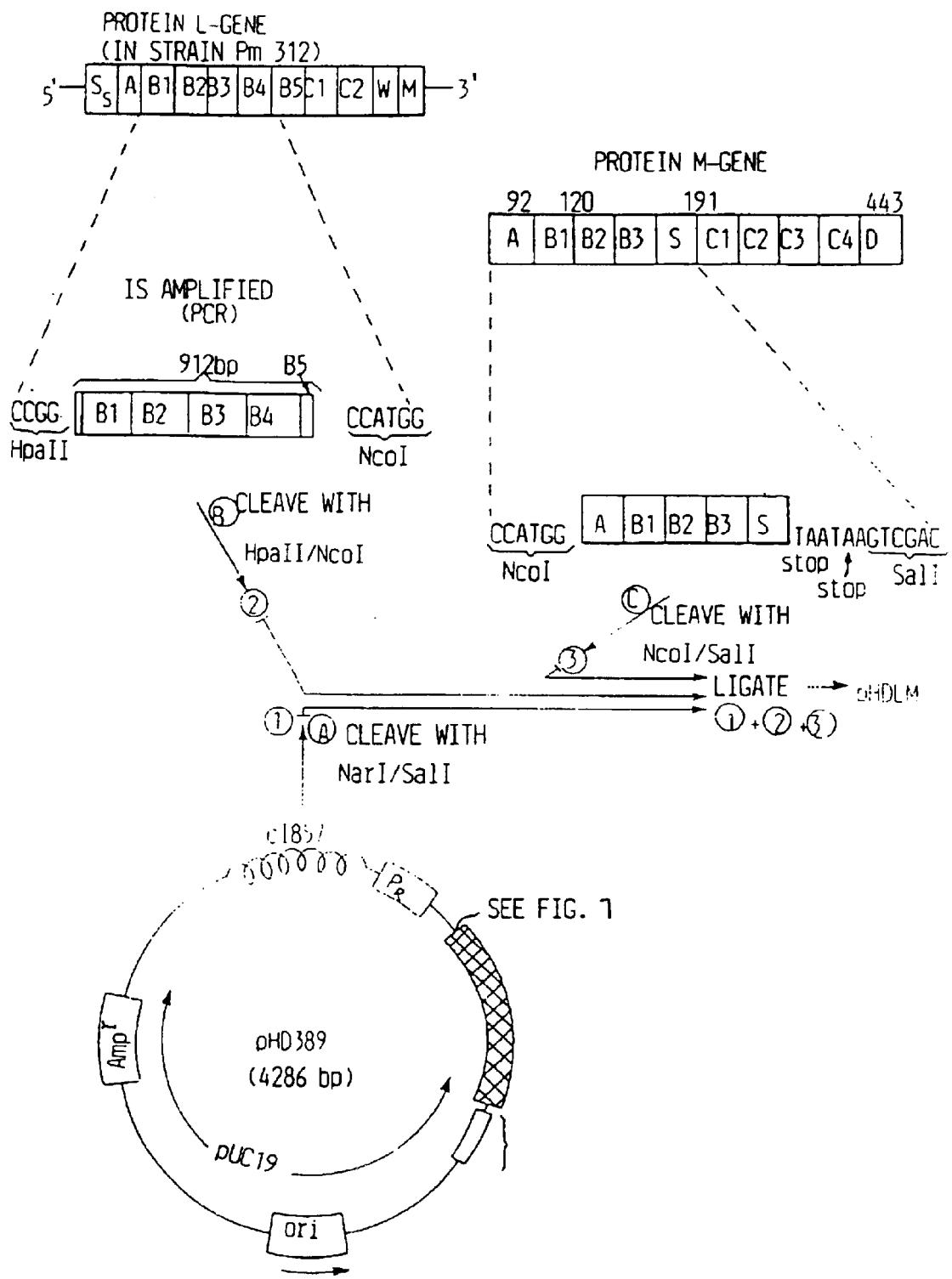
FIG.5b SCHEMATIC OVERALL VIEW OF THE PRODUCTION OF PROTEIN LM

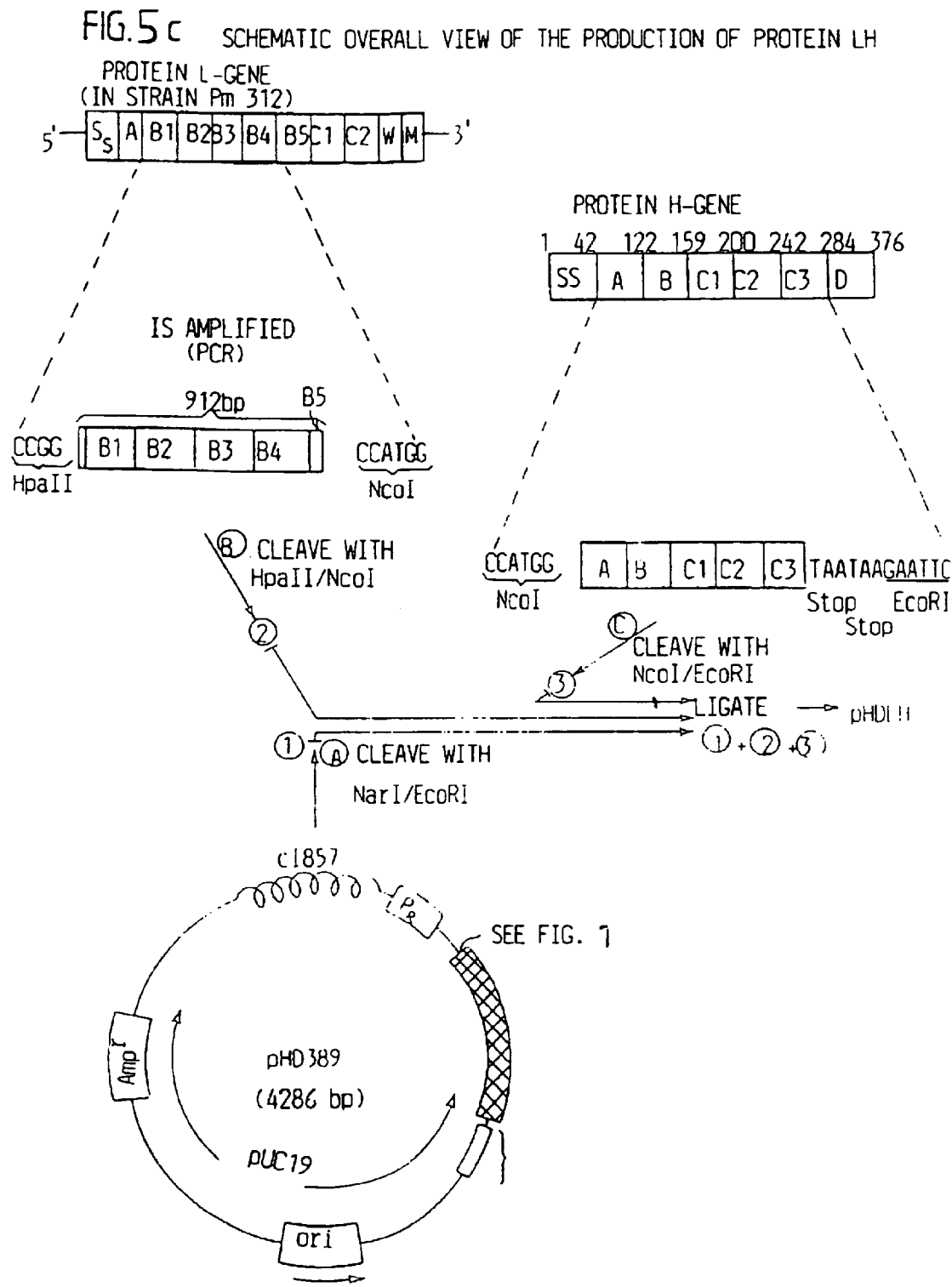

FIG. 6

PROTEIN A: Ss (1–37) | E (37–93) | D (93–154) | A (154–212) | B (212–270) | C (270–328) | X (328–524)

PROTEIN G: Ss (1–34) | E (34–117) | A1 (117–141) | B1 (141–192) | A2 (192–216) | B2 (216–267) | A3 (267–291) | S (291–303) | C1 (303–358) | D1 (358–373) | C2 (373–428) | D2 (428–443) | C3 (443–498) | W (498–568) | M (568–593)

PROTEIN H: Ss (1–42) | A (42–122) | B (122–159) | C1 (159–200) | C2 (200–242) | C3 (242–284) | D (284–376)

M1 PROTEIN: A (1–92) | B1 (92–120) | B2 (120–154) | B3 (148–153) | S (154–191) | C1 (191–233) | C2 (233–275) | C3 (275–318) | C4 (318–339) | D (339–443)

```
GAAAAAGATTAGCAAACTTGACTGCTGAACTTGATAAGGTTAAAGAAGAAAAACAAATC      840
GluLysAspLeuAlaAsnLeuThrAlaGluLeuAspLysValLysGluGluLysGlnIle     280

TCAGACGCAAGCCGTCAACGGCTTCGCCGTGACTTGGACGCATCACGTGAAGCTAAGAAA     900
SerAspAlaSerArgGlnArgLeuArgLeuArgAspAlaSerArgLeuAspHisArgGluAlaLysLys 300

CAAGTTGAAAAAAGCTTTAGAAGAAGCAAACAGCAAATTAGCTGCTCTTGAAAAACTTAAC    960
GlnValGluLysSerLeuGluGluAlaAsnSerLysLeuLeuAlaLeuGluLysLeuAsn     320

AAAGAGCTTGAAGAAGCAAGAAATTAACAGAAAAAGAAAAAGCTGAACTACAAGCAAAA     1020
LysGluLeuGluGluSerLysLysLysLeuThrGluLysGluLysAlaGluLeuGlnAlaLys 340

CTTGAAGCAGAAGCAAAAGCACTCAAAGAACAATTAGCGAAACAAGCTGAAGAACTCGCA    1080
LeuGluAlaGluAlaLysAlaLeuLysGluGlnLeuAlaLysGlnAlaGluGluLeuAla    360

AAACTAAGAGCTGGAAAAGCATCAGACTCACAAACCCCTGATACAAAACCAGGAAACAAA    1140
LysLeuArgAlaGlyLysAlaSerAspSerGlnThrProAspThrLysProGlyAsnLys    380

GCTGTTCCAGGTAAAGGTCAAGCACCACCAGGACAGTTACCATCAACAGGTGAAACAGCA    1200
AlaValProGlyLysGlyGlnAlaProProGlyGlnLeuProSerThrGlyGluThrAla    400

CCAATGAAGGAAAACTAAGAGAAGACAGTTACCATCAACAGGTGAAACAGCTAACCCTTC    1260
ProMetLysGluAsnLysArgGlnLeuProSerThrGlyGluThrAlaAsnProPhePhe    420

ACAGCGGCACGCGTTACTGTTATGGCAACAGCTGGAGTAGCAGCAGTGTAAAAACGCAAA    1320
ThrAlaAlaArgValThrValMetAlaThrAlaGlyValAlaAlaAlaValLysArgLys    440

GAAGAAAACTAA     1329
GluGluAsn***     443
```

```
                                                                    V
GAGCAGCTAACGATCGAAAAAGCAAAACTTGAGGAAGAAAAACAAATCTCAGACGCAAGT        600
GluGlnLeuThrIleGluLysAlaLysLeuGluGluLysGlnIleSerAspAlaSer           200
                                    190
     V                          V
CGTCAAAGCCTTCGTCGTTGACTTGGACGCATCACGTGAAGCTAAGAAACAGGTTGAAAAA       660
ArgGlnSerLeuArgArgAspLeuAspAlaSerArgGluAlaLysLysGlnValGluLys        220
     V                          V
GATTTAGCAAAACTTGACTGCTGAACTTGATAAGGTTAAAGAAGACAAACAAATCTCAGAC       720
AspLeuAlaAsnLeuThrAlaGluLeuAspLysValLysGluAspLysGlnIleSerAsp        240
     V                          V
GCAAGCCGTCAAGCTTCGCCGTGACTTGGACGCATCACGTGAAGCTAAGAAAACAGGTT         780
AlaSerArgGlnArgLeuArgArgAspLeuAspAlaSerArgGluAlaLysLys.
```

FIG.7 (CONT.)

Amino acid sequence and nucleic acid sequence for protein M1. IgG-binding somewhere between amino acid 1-190.

PROTEIN L AND HYBRID PROTEINS THEREOF

BACKGROUND OF THE INVENTION

1. Field of the Invention

The present invention relates to sequences of protein L which bind to light chains of immunoglobulins. The invention also relates to hybrid proteins of protein L having the ability to bind to light chains of all Ig and also to bind to light and heavy chains of immunoglobulin G, DNA-sequences which code for the proteins vectors that contain such DNA-sequences, host cells transformed by the vectors, methods for preparing the proteins, reagent apparatus for separating and identifying immunoglobulins, compositions and pharmaceutical compositions which contain the proteins.

2. Description of the Related Art

The invention relates in particular to the DNA-sequence and to the amino acid sequence of the light-chain forming domains of protein L.

Proteins which bind to the constant domains (of high affinity) of the immunoglobulins (Ig) are known. Thus, protein A (from *Staphylococcus aureus*) (Forsgren, A. and Sjöquist, J. (1966) Protein A from *staphylococcus aureus*. I. Pseudo-immune reaction with human gamma-globulin. J. Immunol. 97: 822–827) binds to IgG from various mammal species. The binding of protein A to IgG is mediated essentially via surfaces in the Fc-fragment of the heavy chain of the IgG-molecule, although a certain bond is also effected with surfaces in the Fab-fragment of the IgG. Protein A lacks the ability of binding to human IgG3 and neither will it bind to IgG from several other animal species, such as important laboratory animals, for instance rats and goats, which limits the use of protein A.

Protein G (Björck, L. and Kronvall, G. (1984) Purification and some properties of streptococcal protein G, a novel IgG-binding reagent. J. Immunol. 133: 969–974; Reis, K., Ayoub, E. and Boyle, M. (1984) Streptococcal Fc receptors. I. Isolation and partial characterization of the receptor from a group C streptococcus. J. Immunol. 132: 3091–3097) binds to heavy chains in human IgG and to all four of its subclasses and also to IgG from most mammals, including rats and goats.

Protein H (Åkesson, P., Cooney, J., Kishimoto, F. and Björck, L. (1990) Protein H—a novel IgG binding bacterial protein. Molec. Immun. 27: 523–531) binds to the Fc-fragment in IgG from human beings, monkeys and rabbits. However, the bond is weaker than in the case of protein G and A, which may be beneficial when wishing to break the bond with a weak agent, for instance when purifying proteins which are readily denatured with the aid of antibodies.

Protein M (Applicant's Patent Application PCT/SE 91100447) binds to the Fc-fragment in IgG from humans, monkeys, rabbits, goats, mice and pigs.

Protein L (Björck, L. (1988) Protein L, a novel bacterial cell wall protein with affinity to Ig L chains. J. Immunol. 140: 1194–1197), which binds to the light chains in immunoglobulins from all of the classes G, A, M, D and E is known (U.S. Pat. No. 4,876,194). The amino acid sequence and the binding domains of this protein, however, have hitherto been unknown.

The aforesaid proteins can be used in the analysis, purification and preparation of antibodies and for diagnostic and biological research.

The elimination of immunoglobulins, with the aid of plasmapheresis, can have a favourable effect on some autoimmune diseases. A broadly binding protein would be an advantage when wishing to eliminate all classes of antibodies in this context.

It has long been known that infectious conditions can be prevented or cured with the introduction of an immune serum, i.e. a serum which is rich in antibodies against the organism concerned or its potentially harmful product. Examples hereof are epidemic jaundice, tetanus, diphtheria, rabies and generalized shingles. Antibodies against a toxic product may also be effective in the case of non-infectious occasioned conditions. Serum produced in animals against different snake venoms is the most common application in this respect. However, the administration of sera or antibody preparations is not totally without risk. Serious immunological reactions can occur in some cases. Singular cases of the transmission of contagious diseases, such as HIV and hepatitis through the agency of these products have also been described. In order to avoid these secondary effects, it has been desirable to produce therapeutic antibodies in test tubes. A large number of novel techniques for the preparation of antibodies in test tubes have been proposed in recent years. Examples of such techniques are hybridom techniques, synthesis of chima-antibodies and the preparation of antibodies in bacteria. These techniques also enable antibodies to be specially designed which can further widen the use of such molecules as therapeutics, for instance in the case of certain tumour-diseases. In the case of some of these novel methods, however, the product totally lacks the Fc-fragment to which all of the described IgG-binding proteins, with the exception of protein L, bind. There is consequently a need of a process for purifying antibodies for therapeutic use, wherein proteins which have a broad binding activity/specificity, can be of value.

It has long been possible to utilize the antibody reaction with its high grade specificity for diagnosing past or, in some cases, ongoing infections with different parasites. This indirect method of indicating infectious agents is called serology and, in many cases, may be the only diagnostic alternative. In certain cases, it can also be of interest to exhibit specific IgE- or IgA-antibodies. When diagnosing with the aid of serology, the antigen is most often fastened to a solid phase, whereafter serum taken from the patient is incubated with the antigen. Antibodies that have been bound from the patient can then be detected in different ways, often with the aid of a secondary antibody (for instance, an antibody which is directed against the light chains of human antibodies) to which an identifiable label has been attached, such as alkaline phosphatase, biotin, radioactive isotopes, fluorescein, etc. In this context, a protein having a broad Ig binding capacity can be used as an alternative to secondary antibodies.

There are a number of non-therapeutic and non-diagnostic reasons for the necessity to bind antibodies. Antibodies are often used in research, both for detection and for purifying the antigen against which they are directed. All techniques which facilitate the purification of antibodies and, in particular, techniques which enable different classes to be purified, are of interest in this context.

Consequently, there is a serious need of a protein which has a broad binding activity/specificity and which binds to several different classes of immunoglobulins from different animal species. At present, there is no known protein which will bind to all immunoglobulin classes. The earlier known proteins A, G, H and M bind only to heavy chains in IgG.

BRIEF SUMMARY OF THE INVENTION

The known protein L (Björck et al, 1988) binds to the light χ-chains and γ-chains in immunoglobulins of all classes, although the bonds are much weaker on the κ-chains. Applicant has charted protein L, has determined the amino acid sequence for protein L, has identified the light-chain binding domains on protein L, and has used these to produce hybrid proteins which possess the IgG-Fc-binding domains of protein G. The Applicant is able to show through protein LG that a protein of broader binding activity/specificity can be produced thereby. The aforesaid proteins A, G. H and M bind to the same surfaces, or to very closely lying surfaces on IgG-Fc. The protein L which binds to light chains can thus be combined with any other functionally similar protein which binds to the Fc-fragment of heavy chains. A similar broadening of the Ig-binding activity is achieved with all alternatives.

BRIEF DESCRIPTION OF THE SEVERAL VIEWS OF THE DRAWINGS

FIG. 1 illustrates the plasmid pHD389; the ribosomal binding sequence, the sequence for the signal peptide from ompA and recognition sequence for several restriction enzymes are shown (SEQ ID NO: 14);

FIG. 2 illustrates the amino acid (SEQ ID NO: 3) and nucleic acid sequence (SEQ ID NO: 4) for protein LG.

FIGS. 5a, 5b and 5c are schematic overall views of the production of the hybrid proteins LA, LM and LH respectively.

FIG. 6 is a schematic inclusive illustration of protein A, G, H, and M1. IgGFc-binding domains are for protein A: E, D, A, B and C; for protein G: C1, C2 and C3; for protein H: A and/or B; and for protein M1: A, B1, B2, B3 and S.

FIG. 7 illustrates the amino acid (SEQ ID NO: 6) and nucleic acid sequence (SEQ ID NO: 5) for protein M1.

Figure 3:
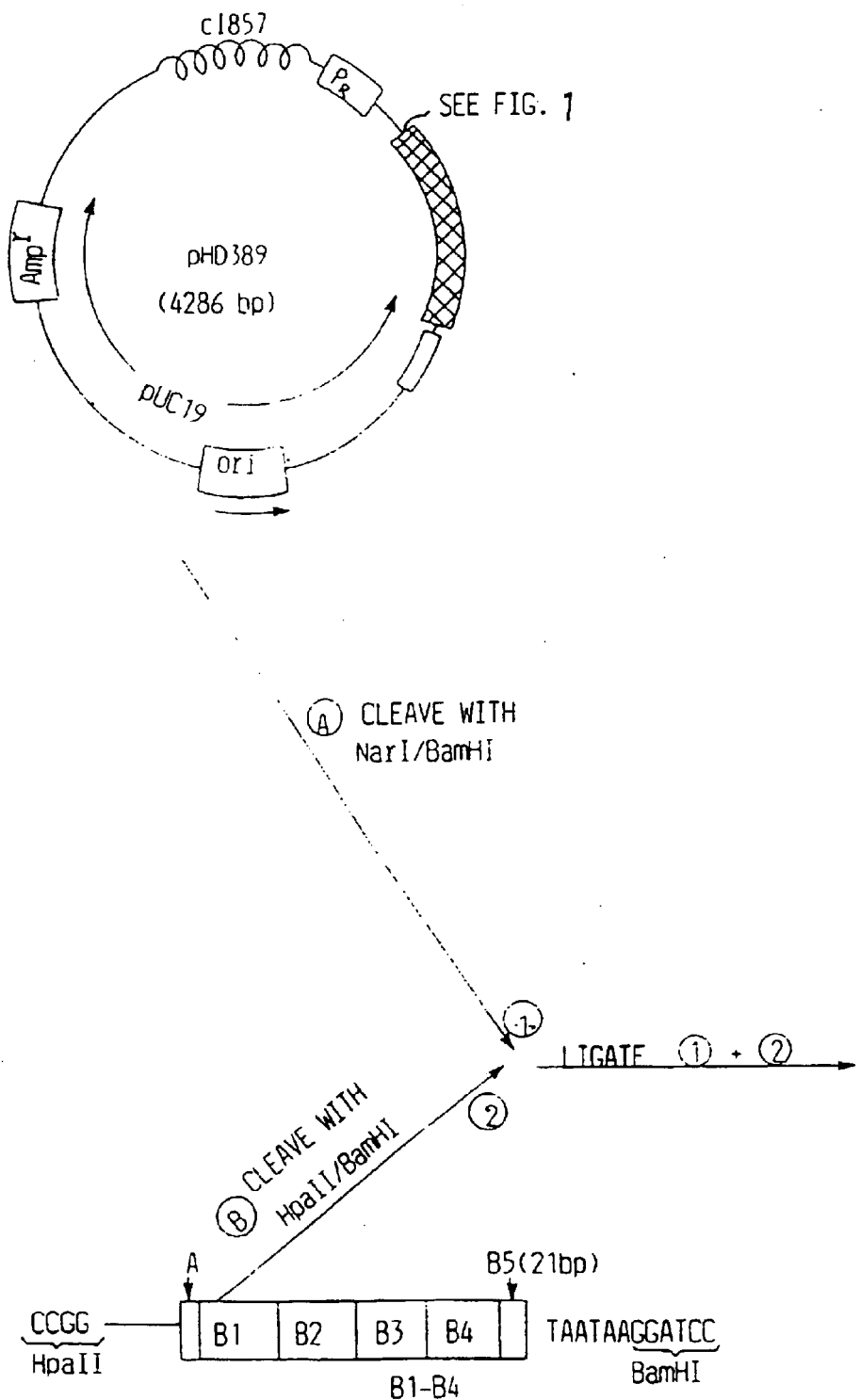
FIG. 3 is a schematic-overall view of the production of protein L.
Figure 3:
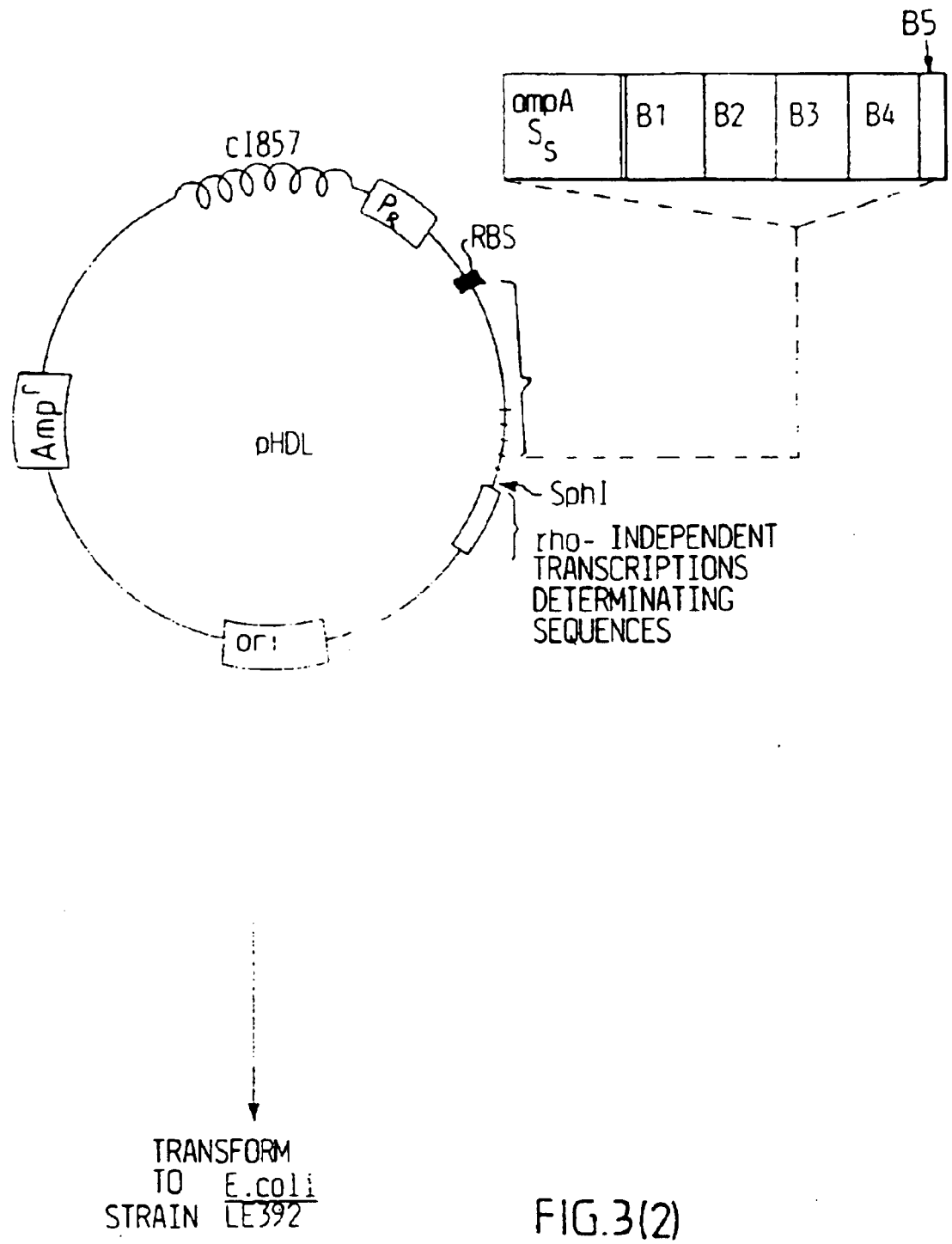
Figure 4:
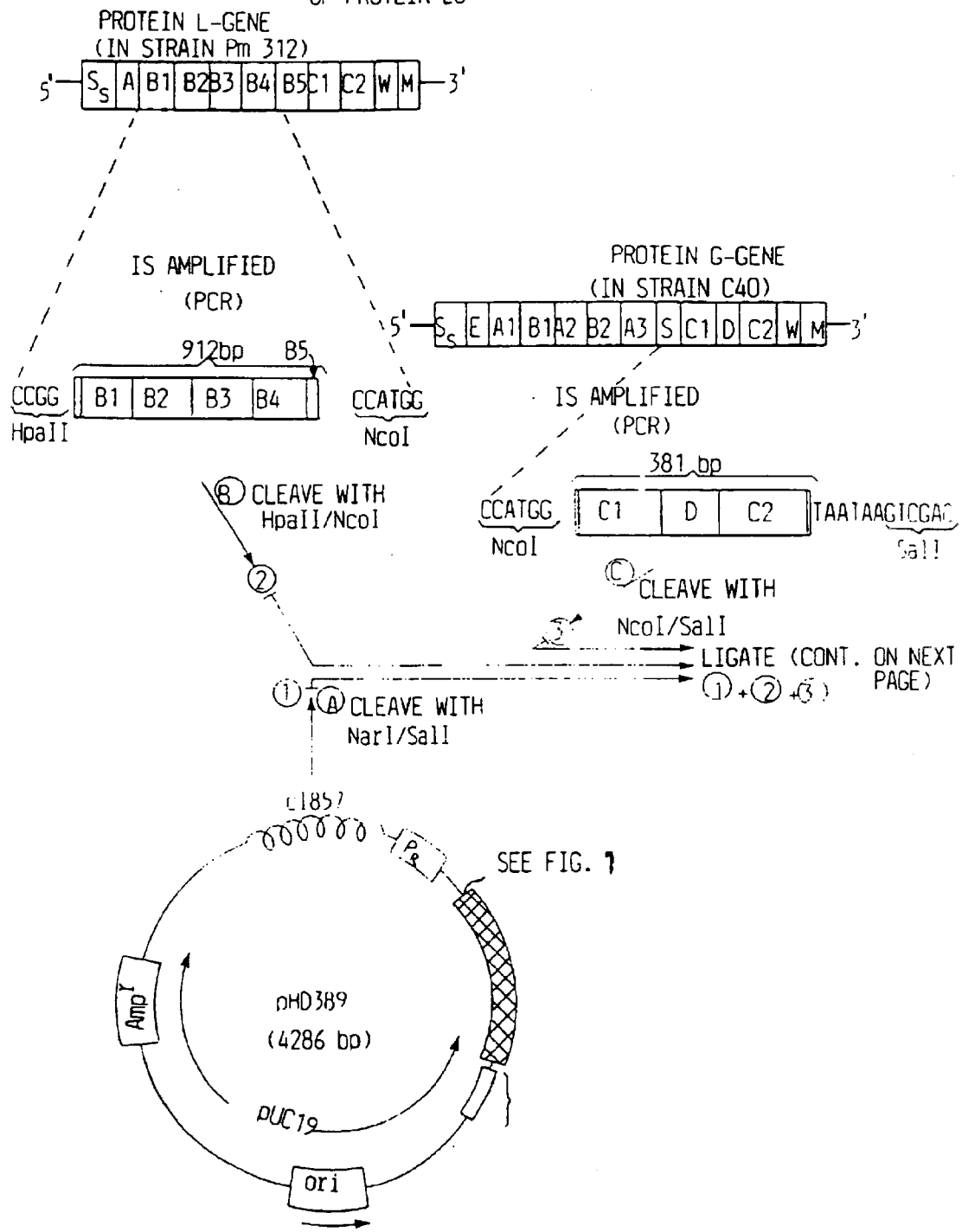
FIG. 4 is a schematic overall view of the production of protein LG.
Figure 4:
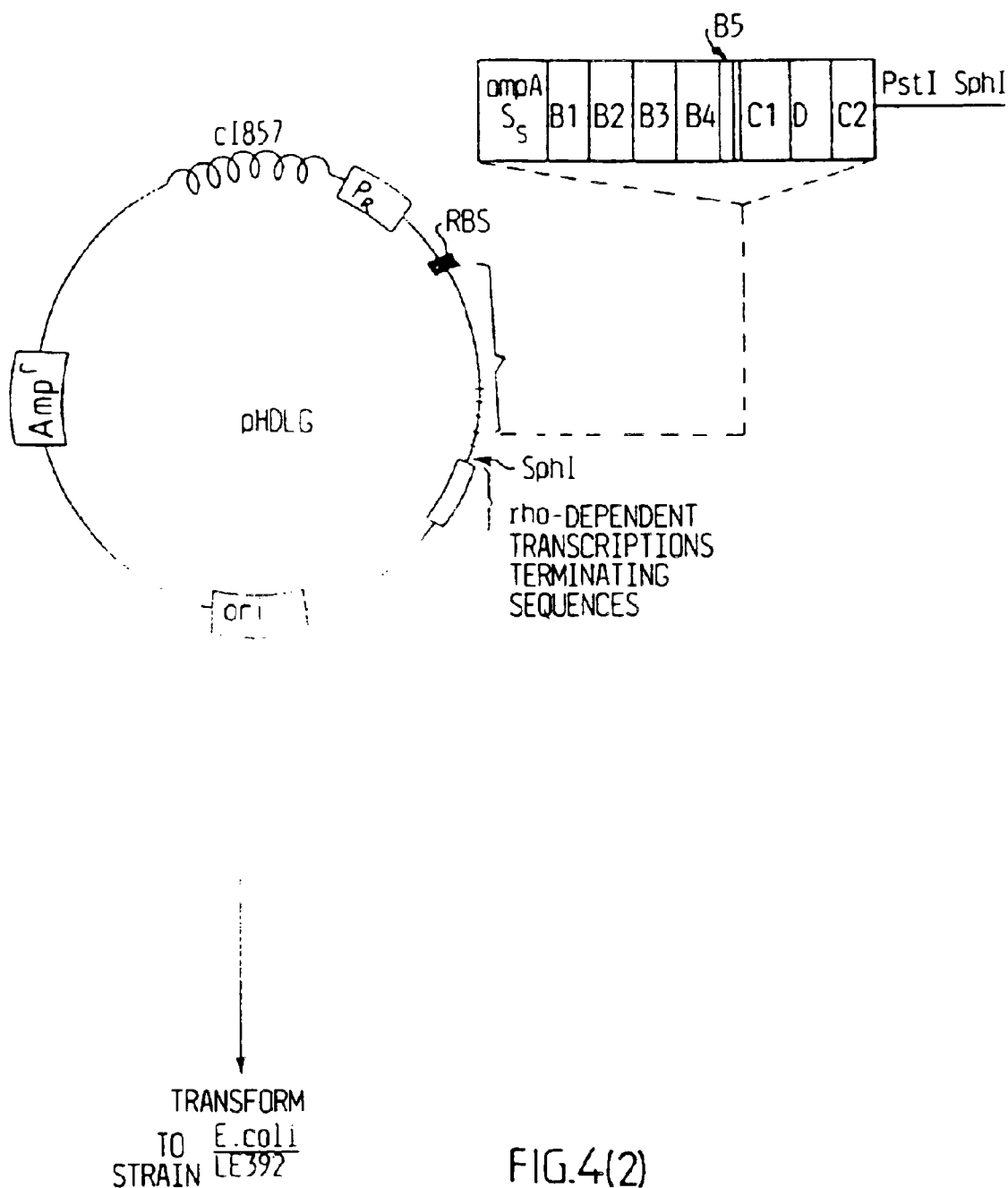

The amino acid and nucleic acid sequence of the light-chain binding domains of protein L is illustrated in FIG. 2.

It will be observed that the drawings are not to scale.

DETAILED DESCRIPTION OF THE INVENTION

Thus, the present invention relates to the sequence of protein L which binds to light chains in Ig and has the amino acid sequence disclosed in FIG. 1, and variants, subfragments, multiples or mixtures of the domains B1–B5 having the same binding properties. The invention also relates to a DNA-sequence which codes for such protein sequences, for instance the DNA-sequence in FIG. 1.

The invention is concerned with a hybrid protein which is characterized by comprising domains which bind to the light χ-chains and λ-chains in immunoglobulins of all classes, and also comprises domains which bind to heavy chains in immunoglobulin G, wherein those domains which bind to the light chains are chosen from among the B1-, B2-, B3-, B4- and B5-domains in protein L and those domains which bind to heavy chains of immunoglobulins are chosen from the C1-, C2- and C3-domains in protein G; the A-, B- and C1-domains from protein H; the A-, B1-, B2- and S-domains in protein M1or the E-, D-, A-, B- and C-domains in protein A (see FIG. 6) and variants, subfragments, multiples or mixtures of these domains that have the same binding properties which bind to heavy chains of immunoglobulins.

By subfragment is meant a part-fragment of the given domains or fragments which include parts from the various domains having mutually the same binding properties. By variants is meant proteins or peptides in which the original amino acid sequence has been modified or changed by insertion, addition, substitution, inversion or exclusion of one or more amino acids, although while retaining or improving the binding properties. The invention also relates to those proteins which contain several arrays (multiples) of the binding domains or mixtures of the binding domains with retained binding properties. The invention also relates to mixtures of the various domains of amino acid sequences having mutually the same binding properties.

The invention relates in particular to a hybrid protein designated LG, and is characterized in that the hybrid protein includes the B-domains in protein L which bind to the light chains in immunoglobulins, and the C1-domains and C2-domains in protein G which bind to heavy chains and have the amino acid sequence disclosed in FIG. 2. The invention also relates to variants, subfragments, multiples or mixtures of these domains.

Protein LG is a hybrid protein having a molecular weight of about 50 kDa (432 amino acids) and comprising four domains, each of which binds to light chains in immunoglobulins, and two IgG-binding domains from protein G. The hybrid protein combines a broad IgG-binding activity, deriving from the high-grade binding ability of protein G to the Fc-fragment of the heavy chain on IgG with the ability of the protein L to bind to light chains of all classes of immunoglobulins. Thus, protein LG binds polyclonal human IgG, IgM, IgA, IgD and IgE. The affinity for human polyclonal IgG is $2\times10^{10}M^{-1}$. All four human immunoglobulin classes are bound. Binding to human IgG is effected with both the κ-and the λ-chain. Both the Fc-fragment and the Fab-fragment of IgG are bound to the hybrid protein. The protein also binds a human IgA-, IgD-, IgE- and IgM-antibodies. The bond is stronger to human immunoglobulins which carry χ than to those which carry the λ-isotope of light chains. IgG from most mammals will be bound by protein LG, thus also IgG from goats and cows, which do not bind to protein L. However, rabbit-IgG which binds relatively weakly to protein L will bind well to the fusion protein. IgM and IgA-antibodies from mice, rats and rabbits will be bound to the protein. Protein LG is highly soluble. It is able to withstand heat and will retain its binding properties even at high temperatures. The binding properties also remain in a broad pH-range of 3–10. The protein withstands detergent and binds marked or labelled proteins subsequent to separation in SDS-PAGE and transference to membranes with elektroblotting. The protein can be immobilized on a solid phase (nitrocellulose, Immobilon®, polyacrylamide, plastic, metal and paper) without losing its binding capacity. The binding properties are not influenced by marking with radioactive substances, biotin or alkaline phosphatase. (The binding abilities of the protein LG are disclosed in Example 3).

The protein comprises 432 amino acids and has a molecular weight of 50 kDa deriving therefrom. The sequence is constructed of an ala sequence of the three last amino acids in the A-domain of the protein L (val-glu-asn), this ala sequence being unrelated to the two proteins, whereafter the four mutually high-grade homologous B-domains from protein L follow. The first of the B-domains is comprised of 76 amino acids, and the remaining domains are each comprised of 72 amino acids. The first nine amino acids from the fifth B-domain are included and followed by two non-related amino acids (pro-met). The protein G-sequences then follow. The last amino acid in the so-called S-domain from protein G is followed by an IgG-binding domain from protein G (C1; 55 amino acids), the intermediate D-region (15 amino acids) and the second IgG-binding C-domain (C2; 55 amino acids). The last amino acid is a methionine, which occurs in natural protein G as the first amino acid in the so-called W-region.

The invention also relates to DNA-sequences which code for the aforesaid proteins.

Figure 7:
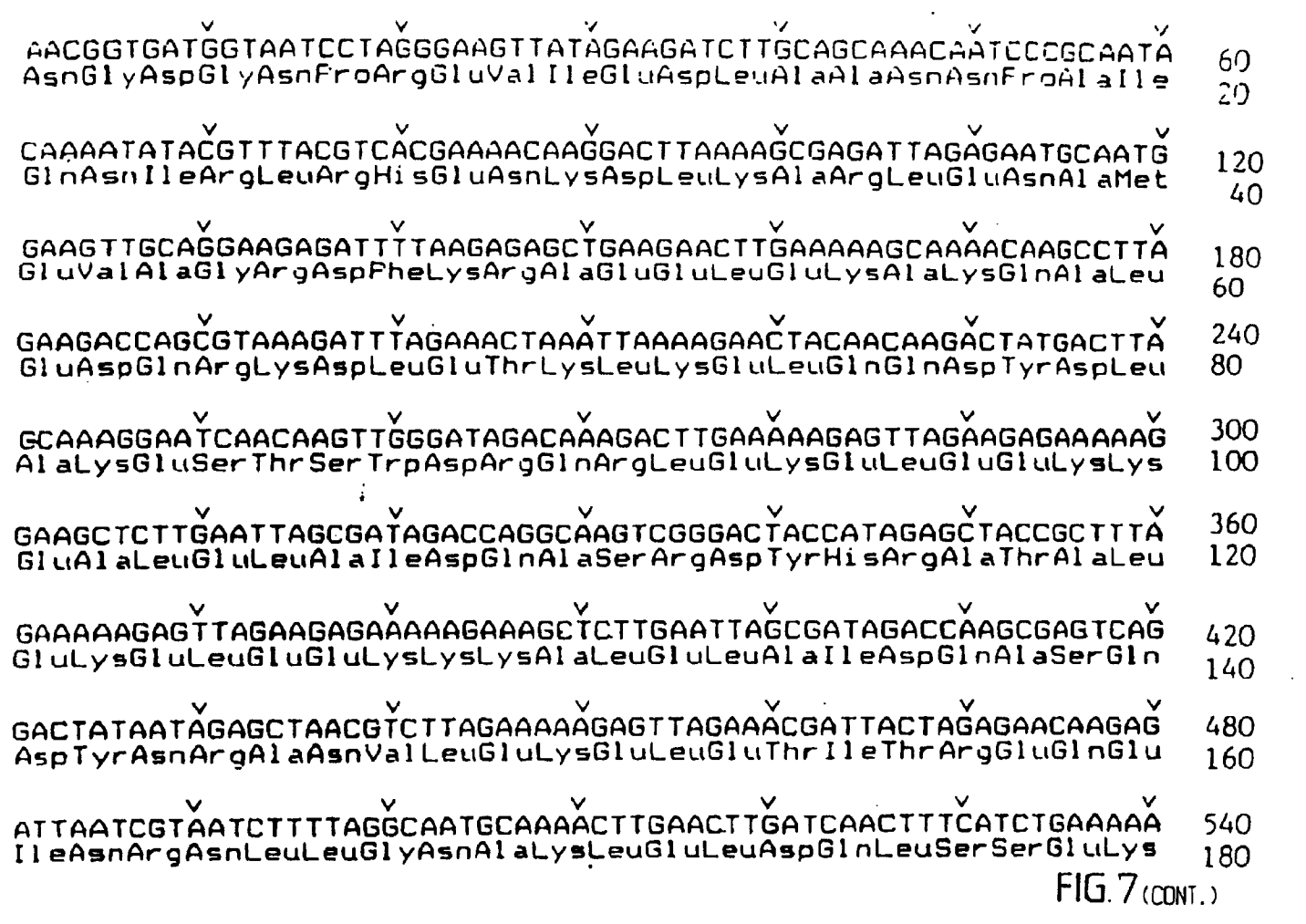

The gene which codes for the IgG-binding amino acid sequences can be isolated from the chromosomal DNA from *Staphylococcus aureus* based on the information on the DNA-sequence for protein A (S. Löfdahl, B. Guss, M. Uhlen, L. Philipsson and M. Lindberg. 1983. Gene for *staphylococcal* protein A. Proc. Natl. Acad. Sci. USA. 80: 697–701) and FIG. 6, or from *G-streptococcus*, preferably strain G 148 or *C-streptococcus*, preferably strain *Streptococcus equisimilis* C 40, based on the information on protein G (B. Guss, M. Eliasson, A. Olsson, M. Uhlen, A.-K. Frej, H. Jörvall, I. Flock and M. Lindberg. 1986. Structure of the IgG-binding regions of *streptococcal* protein G. EMBO. J. 5: 1567–1575) and FIG. 6, or from group *A-streptococcus*, e.g. *S. pyogenes* (type M1) based on the information on the DNA-sequence for protein H (H. Gomi, T. Hozumi, S. Hattori, C. Tagawa, F. Kishimoto and L. Björck. 1990. The gene sequence and some properties of protein H—a novel IgG binding protein J. Immunol. 144: 4046–4052) and FIG. 6, or from the chromosomal DNA in group *A-streptococcus* type M1 based on the information on the DNA-sequence for protein M (Applicant's Patent Application, PCT/SE 91100447) and FIGS. 6 and 7. The gene which codes for the protein that binds to light chains can be isolated from the chromosomal DNA from *Peptostreptococcus magnus* 312 based on the information on the DNA-sequence for protein L in FIG. 2.

By using the chromosomal DNA obtained from the aforesaid bacteria as a template, a DNA-fragment defined with the aid of two synthetic oligonucleotides can then be specifically amplified with the aid of PCR (Polymerase Chain Reaction). This method also enables recognition sites to be incorporated for restriction enzymes in the ends of the amplified fragments (PCR technology, Ed: PCR Technology. Principles and Applications for DNA Amplification. Ed. Henry Erlich. Stockton Press, New York, 1989). The choice of recognition sequences can be adapted in accordance with the vector chosen to express the fragment or the DNA-fragment or other DNA-fragments with which the amplified fragment is intended to be combined. The amplified fragment is then cleaved with the restriction enzyme or enzymes concerned and is combined with the fragment/the other fragments concerned and the fragments are then cloned together in the chosen vector (in this case, the expression vector) (Sambrook, J. E. Fritsch and T. Maniatis, 1989, Molecular cloning: A laboratory manual, 2nd Ed. Cold Spring Harbor Laboratories, Cold Spring Harbor, N.Y., USA). The plasmid vector pHD313 can be used (Dalböge, H. E. Bech Jensen, H. Töttrup, A. Grubb, M. Abrahamson, I. Olafsson and S. Carlsen, 1989. High-level expression of active human cystatin C in *Escherichia coli*. Gene, 79: 325–332), alternatively one of the vectors in the so-called PET-series (PET 20, 21, 22, 23) retailed by Novagen (Madison, Wis., USA).

The hybrid proteins are then incorporated in an appropriate host, preferably *E. coli*. The invention also relates to such hosts as those in which the hybrid proteins are incorporated.

Those clones which produce the desired proteins can be selected from the resultant transformants with the aid of a known method (Fahnestock et al., J. Bacteriol. 167, 870 (1986).

When the proteins that can bind to the light chains in the immunoglobulins and to the heavy chains in IgG have been purified from the resultant positive clones with the aid of conventional methods, the binding specificities of the proteins are determined for selection of those clones which produce a protein that will bind to the light chains in immunoglobulins and to the heavy chains in IgG.

Subsequent to having isolated plasmid DNA in said clone with conventional methods, the DNA-sequence in the inserted material is determined with known methods (Sanger et al., Proc. Natl. Acad. Sci. USA 74, 5463 (1977).

The invention also relates to DNA-sequences which hybridize with said identified DNA-sequences under conventional conditions and which code for a protein that possesses he desired binding properties. Strict hybridizing conditions are preferred.

Expression of the genes can be effected with expression vectors which have the requisite expression control regions, the structural gene being introduced after said regions. As illustrated in FIG. 1 and claim 2, the structural gene can be used for protein LG or other hybrid proteins with protein L.

With regard to expression vectors, different host-vector-systems have been developed, of which the most suitable host-vector-systems can be selected for expression of the genes according to the present invention.

The present invention also relates to a method of producing the inventive hybrid proteins by cultivating a host cell which is transformed with an expression vector in which DNA which codes for the proteins according to the invention is inserted.

This method includes the steps of
(1) inserting into a vector a DNA-fragment which codes for the hybrid proteins;
(2) transforming the resultant vector into an appropriate host cell;
(3) cultivating the resultant, transformed cell for preparation of the desired hybrid protein; and
(4) extracting the protein from the culture.

In the first step, the DNA-fragment which codes for the hybrid protein is inserted in a vector which is suitable for the host that is to be used to express the hybrid protein. The gene can be inserted by cleaving the vector with an appropriate restriction enzyme, and then legating the gene with the vector.

In the second step, the vector with the hybrid plasmid is inserted into host cells. The host cells may be *Escherichia coli. Bacillus subtilis* or *Saccharomyces cerevisiae* or other suitable cells. Transformation of the expressions hybrid vector into the host cell can be effected in a conventional manner and clones which have been transformed can then be selected.

In the third step, the obtained transformants are cultivated in an appropriate medium for preparation of the desired proteins by expression of the gene coded for the hybrid protein.

In the fourth step, the desired protein is extracted from the culture and then purified. This can be achieved with the aid of known methods. For instance, the cells can be lysed with the aid of known methods, by treating the cells with ultrasonic sound, enzymes or by mechanical degradation. The protein which is released from the cells or which excretes in the medium can be recovered and purified with the aid of conventional methods often applied within the biochemical field, such as ion-exchange chromatography, gel filtration, affinity chromatography with the use of immunoglobulins as ligands, hydrophobic chromatography or reverse-phase chromatography. These methods can be applied individually or in suitable combinations.

As mentioned previously, the inventive proteins may be used for binding, identifying or purifying immunoglobulins. They can also be bound to pharmaceuticals and used in formulations which have delayed release properties. To this end, the protein may be present in a reagent appliance for pharmaceutical composition in combination with appropriate reagents, additives or carriers.

The proteins can be handled in a freeze-dried state or in a PBS-solution (phosphate-buffered physiological salt solution) pH 7.2 with 0.02% $NaN_3$. It can also be used connected to a solid phase, such as carbohydrate-based phases, for instance CNBr-activated sepharose, agarose, plastic surfaces, polyacrylamide, nylon, paper, magnetic spheres, filter, films. The proteins may be marked with biotin, alkaline phosphatase, radioactive isotopes, fluorescein and other fluorescent substances, gold particles, ferritin, and substances which enable luminescence to be measured.

Other proteins may also be used as carriers. These carriers may be bound to or incorporated in the proteins, in accordance with the invention. For instance, it is conceivable to consider the whole of proteins A, G, H, M as carriers for inserted sequences of protein L which bind to light chains. In turn, these carriers can be bound to the aforesaid carriers.

The pharmaceutical additions that can be used are those which are normally used within this field, such as pharmaceutical qualities of mannitol, lactose, starch, magnesium stearate, sodium saccharate, talcum, cellulose, glycose, gelatine, saccharose, magnesium carbonate and similar extenders, such as lactose, dicalcium phosphate and the like; bursting substances, such as starch or derivatives thereof; lubricants such as magnesium stearate and the like; binders, such as starch, gum aribicum, polyvinylpyrrolidone, gelatine, cellulose and derivatives thereof, and the like.

The invention will now be described in more detail with reference to the accompany drawings.

EXAMPLE 1

Cloning and Expression of the IgG-light-chain-binding Domains in Protein L

Construction Of Synthetic Oligonucleotides (Primers) for Amplifying Sequences Coded for Protein L, Domain B1–B4

It has been found that a protein L peptide (expressed in *E. coli*) constructed of the sequence ala-val-glu-asn (SEQ ID NO: 15) domain B1(from protein L) binds to the light chains of the immunoglobulins (W. Kastern, U. Sjöbring and L. Bjˆ orck. 1992. Structure of *peptostreptococcal* protein L and identification of a repeated immunoglobulin light chain-binding domain. J. Biol. Chem. in-print). Since this simple protein L-domain has a relatively low affinity to Ig, ($1 \times 10^7$ $M^{-1}$), and since the naturally occurring protein L which is constructed of several mutually similar domains (B1–B5) has a high affinity to Ig ($1 \times 10^{10}$ $M^{-1}$) four of these domains have been expressed together in the following way:

PL-N and PL-C1 are synthetic oligonucleotides (manufactured by the Biomolecular Unit at Lund University (Sweden) in accordance with Applicant's instructions) which have been used to amplify a clonable gene fragment which is amplified with PCR (Polymerase Chain Reaction) and which codes for four Ig-binding protein L domains (ala-val-glu-asn-B1-B2-B3-B4-lys-lys-val-asp-glu-lys-pro-glu-glu, SEQ ID NO: 1). Amino acids in the protein L-sequence are given for the primer which corresponds to the coded strand (PL-N):

PL-N: 5'-GCTCAGGCGGCGCCGGTAGAAAAT AAAGAAGAAACACCAGAAAC-3' (SEQ ID NO: 7)

valgluasnlysglugluthrproglu (SEQ ID NO: 8)

5'-end of this oligonucleotide is homologous with the coded strand in the protein L-gene (emphasized): those codons which code for the last three amino acids in the A-domain (val-glu-asn) are followed by the codons for the first six amino acids in the first of the Ig-binding domains in protein L (B1).

PL-C1: 5'-CAGCAGCAGGATTCTTATTATTCTTCTGGT TTTCGTCAACTTT CTT-3' (SEQ ID NO: 9)

This oligonucleotide is homologous with the opposing non-coding strand in the gene for protein L (the sequence corresponds to the first nine amino acids in domain B5).

DNA-fragments which have been amplified with the aid of PL-N contain the recognition sequence for the restriction enzyme HpaII (emphasized) immediately before the codon which is considered to code for the first amino acid (val) in the expressed protein L-fragment. The fragment which is cleaved with HpaII can be ligated with DNA (in this case, consisting of the used expression vector pHD389) which has been cleaved with the restriction enzyme NarI. The DNA-fragment that has been cleaved with HpaII and ligated with vector pHD389, which has been cleaved with NarI, will be translated in the correct reading frame. The construction results in translation of an additional amino acid (ala) immediately in front of the first amino acid in protein L.

DNA-fragments which have been amplified with the aid of PL-C1 will contain the recognition sequence for the restriction enzyme BamHI (overlined above the sequence) immediately after the sequence which codes for the last amino acid in the expressed protein L-fragment (glu). The vector pHD389 contains a unique recognition sequence for BamHI as part of its so-called multiple cloning sequence which follows the NarI recognition sequence. DNA-fragments which have been amplified with the aid of PL-C1 will include two so-called stop-codons (emphasized) which results in translation of the fragment inserted in the vector to cease.

The sequence which was considered to be amplified contains no internal recognition sequences for the restriction enzymes HpaII or BamHI.

Amplifying and Cloning Procedures (PCR) (Polymerase Chain Reaction) was effected with a protocol described by Saiki, R. D. Gelfand, S. Stoffel, S. Scharf, R. Higuchi, G. Horn, K. Mullis and H. Erlich, 1988; Primer-directed enzymatic amplification of DNA with a thermostable DNA polymerase. Science 239: 487-49127; PCR was effected in a Hybaid Intelligent Heating-block (Teddington, UK): 100 µl of a reaction mixture contained 50 mM KCl, 10 mM Tris-HCl, pH 8.3, 1.5 mM $MgCl_2$, 100 µ/ml gelatine, 300 µM with respect to each of the deoxynucleotides (dATP, dCTP, dGTP, dTTP), (Pharmacia), 20 pmol of each of the oligonucleotides PL-N and PL-C1, 10 µl of a target (template) DNA-solution containing 0.1 mg/ml of chromosomal DNA from *Peptostreptococccus magnus*, species 312. The mixture was covered with mineral oil (Sigma) and DNA was denatured by heating to 98° C. for 10 minutes. 2.5 units of AmpliTaq (Perkin Elmer Cetus, Norwalk, Conn.) were added and PCR was then carried out with 25 cycles consisting of a denaturing step at 94° C. for 1 minute, followed by a hybridizing step at 56° C. for 1 minute, and finally by an extension step at 72° C. for 1 minute. Amplified DNA was analyzed by electrophoresis in agarose gel. The amplified DNA was cleaved with the restriction enzymes HpaII (Promega), (8 units/µg amplified DNA) and BamHI (Promega), (10 units/µg amplified DNA) at 37° C. The thus amplified and subsequently cleaved DNA-product was isolated by electrophoresis in a 2% (weight by volume) agarose gel (NuSieve agarose, FMC Biproducts) in a TAE-buffer (40 Mm Tris, 20 Mm Na-acetate, 2 Mm EDTA, Ph 8.0). The resulting 930 base-pair fragment was cut from the gel. The DNA concentration in this removed gel-piece was estimated to be 0.05 mg/ml. The agarose-piece containing the cleaved, amplified fragment was melted in a water bath at 65° C., whereafter the fragment was allowed to cool to 37° C. 10 µl (0.5 µg) of this DNA was transferred to a semimicrotube (Sarstedt) preheated to 37° C., whereafter 1 µl of the vector pHD389 was immediately added and cleaved with NarI (Promega) and BamHI, 1 µl 10xligas-buffer (Promega and 1 µl T4 DNA-ligase (Promega; 1 unit/µl). The ligating reaction was then used to transform $E.$ $coli$, strain LE392, which had been competent in accordance with the rubidium/calciumchloride-method as described by Kushner (1978). Molecular biological standard methods have been used in the manipulation of DNA (Sambrook, J. E. Fritsch and T. Maniatis, 1989. Molecular cloning: A laboratory manual. 2nd Ed. Cold Spring Harbor Laboratories, Cold Spring Harbor, N.Y., USA). The cleaving and ligating conditions recommended by the manufacturer of DNA-ligase and restriction enzymes have been followed in other respects.

Expression System

The vector pHD389 (see FIG. 2) is a modified variant of the plasmid pHD313 (Dalböge, H. E. Bech Jensen, H. T öttrup, A. Grubb, M. Abrahamson, I. Olafsson and S. Carlsen, 1989. High-level expression of active human cystatin C in $Escherichia$ $coli$. Gene, 79: 325–332). The vector, which is replicated in $E.$ $coli$ (contains ori=origin of replication from plasmid pUC19) is constructed so that DNA-fragments which have been cloned into the cleaving site of NarI will be transcribed and translated downstream of and in the immediate vicinity of the signal peptide (21 amino acids), from envelope-protein ompA from $E.$ $coli$. Translation sill be initiated from the codon ATG which codes for the first amino acid (methionine) in the signal peptide. This construction permits the translated peptide to be transported to the periplasmic space in $E.$ $coli$. This is advantageous, since it reduces the risk of degradation of the desired product of enzymes occurring intracellularly in $E.$ $coli$. Moreover, it is easier to purify peptides which have been exported to the periplasic space. Unique recognition sequences (multiple cloning sequences) for several other restriction enzymes, among them ecoRI, SalI and BamHI are found immediately after the NarI cleaving site. An optimized so-called Shine-Dalgarno-sequence (also called ribosomal binding site, RBS) is found seven nucleotides upstream from the ATG-codon in the signal sequence from ompA, this optimized sequence binding to a complementary sequence in 16S rRNA in the ribosomes and is responsible for the translation being initiated in the correct place. The transcription of such DNA as that which is co-transcribed with the signal sequence for ompA is controlled by the $P_R$-promotor from coliphage λ. The vector also contained the gene for cI857 from coliphage λ whose product down-regulates transcription from $P_R$ (and whose product is expressed constitutively). This cI857-mediated down-regulation of transcription from $P_R$ is heat-sensitive. The transcription regulated from this promotor is terminated with the aid of a so-called rho-independent transcription terminating sequence (forms a structure in DNA which results in the DNA-dependent RNA-polymerase leaving the DNA-strand) which is placed in the vector immediately downstream of the multiple cloning sequence. The plasmid also carries the β-lactamase gene (from the plasmid pUC19) whose product permits ampicillin-selection of $E.$ $coli$ clones that have been transformed by the vector.

Selection of Protein L-producing Clones

Figure 8:
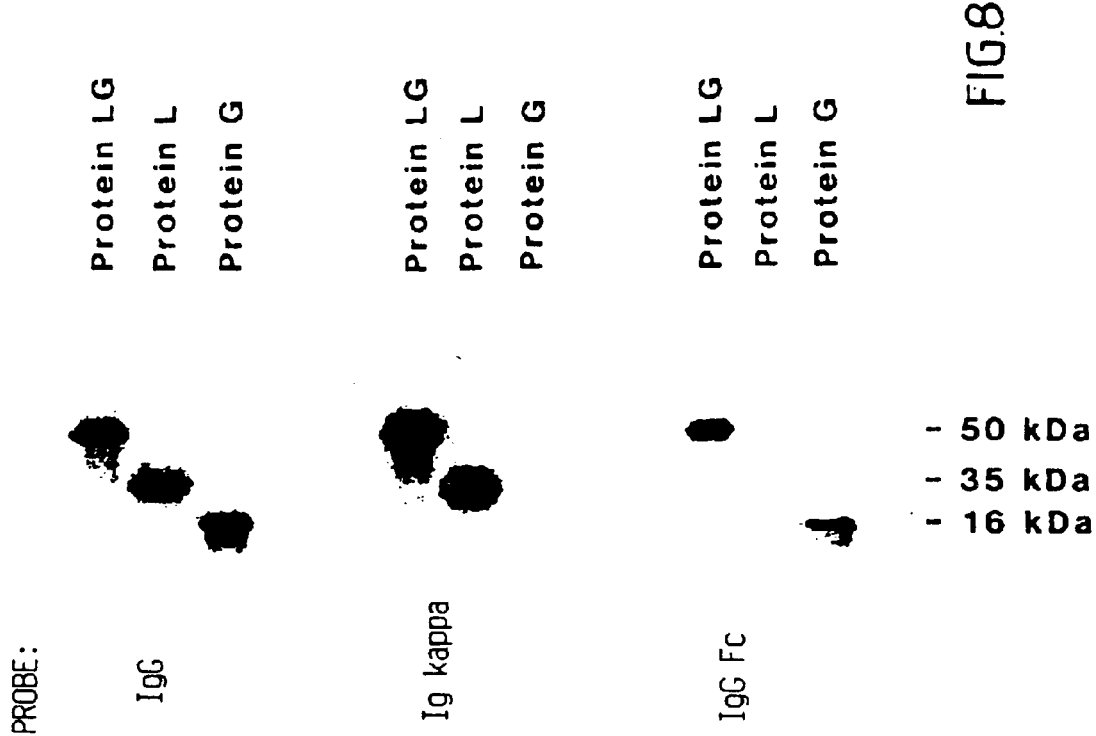
FIG. 8 illustrates Western Blot for protein G, L and LG with certain immunoglobulins and immunoglubulin fragments.

The transformed bacteria are cultivated, or cultured, on culture plates with an LB-medium which also contained ampicillin in a concentration of 100 µg/ml. Cultivation of the bacteria progressed overnight at 30° C., whereafter the bacteria were transferred to an incubator where they were cultivated for a further 4 hours at 42° C. The plates were kept in a refrigerator overnight. On the next day, the colonies were transferred to nitrocellulose filters. Filters and culture plates were marked so as to enable the transferred colonies to be readily identified on respective culture plates. The culture plates were again incubated overnight at 30° C., so that remaining rests of transferred bacteria colonies could again grow. The plates were then kept in a refrigerator. The bacteria in the colonies on the nitrocellulose-impressions were lysed by incubating the filter in 10% SDS for 10 minutes. Filters containing lysed bacteria were then rinsed with a blocking buffer which comprised PBS (pH 7.2) with 0.25% gelatine and 0.25% Tween-20 (four baths, 250 ml each at 37° C.), whereafter the filter was incubated with radioactively marked (marked with $^{125}I$ in accordance with the chloramin-T-method) Ig-κ-chains (20 ng/ml in PBS with 0.1% gelatine). The incubation took place at room temperature over a period of 3 hours, whereafter non-bound radioactively marked was rinsed-off with PBS (pH 7.2) containing 0.5 M NaCl, 0.25% gelatine and 0.25% Tween-20 (four baths, 250 ml each at room temperature). All filters were exposed to X-ray film. Positive colonies were identified on the original culture plate. Clones which reacted with Ig-κ-chains were selected and analyzed with respect to the size on the DNA-fragment introduced in the vector. One of these clones was selected for the production of protein L, pHDL. The DNA introduced from this clone into plasmid pHD389 was sequenced. The DNA-sequence was found to be in full agreement with corresponding sequences (B1-B4 and 21 bases in B5) in the gene for protein L from $Peptostreptococcus$ $magnus$, strain 312. The size and binding properties of the protein produced by clone pHDL was analyzed with the aid of SDS-PAGE (see FIG. 8), dot-blot experiment (see FIG. 9) and competitive binding experiments.

Production of Protein L

Several colonies from a culture plate with $E.$ $coli$ pHDL were used to inoculate a preculture (LB-medium with an addition of 100 mg/l ampicillin), which was cultured at 28° C. overnight. On the following morning, the preculture was transferred to a larger volume (100 times the volume of the preculture) of fresh LB-medium containing ampicillin (100 mg/l) and was cultured in shake-flasks (200 rpm), (or fermentors) at 28° C. The culture temperature was raised to 40° C. (induction of transcription) when the absorbency value at 620 nm reached 0.5. Cultivation then continued for 4 hours (applied solely to cultivation in shake-flasks). Upon completion of the cultivation process, the bacteria were centrifuged down. The bacteria were then lysed with an osmotic shock method at 4° C. (Dalböge et al., 1989 supra). The lysate was adjusted to a pH=7. Remaining bacteria rests were then centrifuged down, whereafter the supernatent was purified on IgG-sepharose in accordance with earlier described protocol for protein G and protein L (U. Sjöbring, L. Björck and W. Kastern. 1991. *Streptococcal* protein G: Gene structure and protein binding properties. J. Biol. Chem. 266: 399–405; W. Kastern, U. Sjöbring and L. Bj örck. 1992. Structure of *peptostreptococcal* protein L and identification of a repeated immunoglobulin light chain-binding domain. J. Biol. Chem. 267 (18):12820–5.

The expression system gave about 20 mg/l of protein L when cultivation in shake-flasks. The culture was deposited at DSSM, Identification Reference DSSM *E. coli* LE392/ pHDL.

EXAMPLE 2

Cloning and Expression of Protein LG
Construction of Oligonucleotides (Primers) for Amplifying Sequences which Code for Protein LG
Protein L It has been found that a protein L-peptide (expressed in *E. coli*) constructed of the sequence ala-val-glu-asn-domain B1 (from protein L) will bind to the light chains of the immunoglobulins (Kastern, Sjöbring and Björck, 1992, J. Biol. Chem. 267 (18):12820–5). Since the affinity of this simple domain to Ig is relatively low ($1\times10^{-7}M^{-1}$) and since the naturally occurring protein L, which is comprised of several mutually similar domains (B1–B5) has a higher affinity to Ig ($1\times10^{10}M^{-1}$), four of these domains have been expressed together in the following way:

PL-N and PL-C2 are synthetic oligonucleotides (manufactured at the Biomolecular Unit at Lund University (Sweden) in accordance with applicant's instructions) which were used, with the aid of PCR (Polymerase Chain Reaction) to amplify a clonable gene fragment, called B1–4, which codes for four Ig-binding protein L domains (ala-val-glu-asn-B1-B2-B3-B4-lys-lys-val-asp-glu-lys-pro-glu-glu, SEQ ID NO: 1).
PL-N: 5'-GCTCAGGCGGCGCCGGTAGAAAATAAAGA AGAAACACCAGAAAC-3' (SEQ ID NO: 7)
valgluasnlysglugluthrproglu (SEQ ID NO: 8)
P1-C2: 5'-CAGCAGCAGCCATGGTTCTTCTGGTTT TTCGTCAACTTTCTTA-3', (SEQ ID NO: 10)

Amino acids have been shown under corresponding triplets in the coded strand. DNA-fragments which have been amplified with the aid of PL-N contain the recognition sequence for the restriction enzyme HpaII immediately upstream of the triplet which codes for the first amino acid (val) in the expressed protein L-fragment. The fragment that has been cleaved with HpaII can be ligated with DNA (in this case, the used expression vector pHD389) which has been cleaved with NarI. The construction results in translation of an extra amino acid (ala) immediately upstream of the first amino acid in the protein L-fragment. The DNA-fragment that has been amplified with the aid of PL-C2 will contain the recognition sequence for the restriction enzyme NcoI (emphasized) immediately downstream of the sequence which codes for the last amino acid in the expressed protein L-fragment (glu). Amplified fragments which have been cleaved with NcoI can be ligated to the NcoI-cleaved, PCR-generated protein-asp-CDC-met-fragment (see below).
Protein G It is known that a simple C-domain from protein G will bind to IgG (B. Guss, M. Eliasson, A. Olsson, M. Uhlen, A.-K. Frej, H. Jörnvall, I. Flock and M. Lindberg. 1986. Structure of the IgG-binding regions of *streptococcal* protein G. EMBO. J. 5: 1567–1575). The strength at which a simple C-domain binds to IgG is relatively low ($5\times10^7 M^{-1}$). A fragment which consists of two C-domains with an intermediate D-region having a length of 15 amino acids, however, has a considerably higher affinity to IgG ($1\times10^9 M^{-1}$). CDC-N and CDC-C are oligonucleotides which have been used as PCR-primers to amplify a clonable DNA-fragment, designated CDC, which codes for two IgG-binding protein G-domains (pro-met-asp-CDC-met).
CDC-N: GGCCATGGACACTTACAAATTAATCCTT AATGGT (SEQ ID NO: 11)
metaspthrtyrlysleuileleuasngly (SEQ ID NO: 12)
CDC-C: CAGGTCGACTTATTACATTTCAGTTACCGT AAAGGTCTTAGT (SEQ ID NO: 13)

Amino acids in the resultant sequence have been shown beneath the primer of the coding strand. DNA-fragments which have been amplified with the aid of CDC-N contain the recognition sequence for the restriction enzyme NcoI (marked with a line above the sequence). Cleaved amplified fragments can be ligated with the fragment that has been amplified with the aid of PL-C2 and then cleaved with NcoI. The fragment will therewith be translated to the correct reading frame. DNA-fragments which have been amplified with the aid of CDC-C will contain two so-called stop codons (emphasized) which terminate translation. The recognition sequence for the restriction enzyme SalI (marked with a line above the sequence) follows immediately afterwards, this sequence also being found in the expression vector pHD389 (see FIG. 1).

Those sequences which code for the binding properties of protein L (B1–B5) and for protein G (CDC) respectively contain no internal recognition sequences for the restriction enzymes HpaII, SalI or NcoI.
Amplification and Cloning Procedures PCR (Polymerase Chain Reaction) was carried out in accordance with a protocol described by Saiki et al., 1988; PCR was carried out in a Hybaid Intelligent Heating-block (Teddington, UK): 100 µl of the reaction mixture contained 50 mM KCl, 10 mM Tris-HCl, pH 8.3, 1.5 mM MgCl$_2$, 100 µg/ml gelatine, 300 µM with respect to each of the deoxy-nucleotides (dATP, dCTP, dGTP, dTTP), (Pharmacia). In order to amplify sequences which code for the light-chain binding parts of protein L, there were added 20 pmol of each of the oligonucleotides PL-N and PL-C2, and 10 µl of a DNA-solution which contained 0.1 mg/ml of chromosomal DNA from *Peptostreptococcus magnus*, strain 312. By way of an alternative, 20 pmol were added to each of the oligonucleotide pairs CDC-N and CDC-C and 10 µl of a DNA-solution which contained 0.1 mg/ml of chromosomal DNA from a group C *streptococcus* strain (*Streptococcus equisimilis*) called C40 (U. Sjöbring, L. Björck and W. Kastern. 1991. *Streptococcal* protein G: Gene structure and protein binding properties. J. Biol. Chem. 266: 399–405 or with NcoI and SalI (10 U/µg PCR-product), (for CDC) at 37° C. The thus amplified and subsequently cleaved DNA-fragments were then separated by electrophoresis in a 2% (weight by volume) agrose gel (NuSieve agarose, FMC Bioproducts) in a TAE-buffer (40 mM Tris, 20 mMNa-acetate, 2 mM EDTA, pH 8.0). The resultant fragments, 930 bp (for B1–4) and 390 bp (for CDC) were cut from the gel. The concentration of DNA in the thus separated gel pieces was estimated to be 0.05 mg/ml. The agarose pieces cut from the gel and containing the cleaved, amplified fragments (B1–4 and CDC) were melted in a water bath at 65° C., whereafter they were allowed to cool to 37° C. 10 µl (0.5 µg)

of this DNA were transferred to a semi-microtube (Sarstedt), preheated to 37° C., whereafter 1 µl of the vector pHD389 which had been cleaved with NarI and SalI were added. 1 µl 10 ×ligase buffer (Promega) and 1 µl T4 DNA-ligase (1 unit/µl) were also added. The ligating reaction was permitted to take place at 37° C. for 6 hours. The cleaving and ligating conditions recommended by the producer of DNA-ligase and restriction enzymes (Promega) were followed in other respects. The ligating reaction was then used to transform E. coli, strain LE392, which had been made competent in accordance with the rubidium-chloride/calcium-dichloride method as described by Kushner (1978). Manipulation of DNA was effected in accordance with molecular biological standard methods (Sambrook et al., 1989).

Expression System

The vector pHD389 (see FIG. 2) is a modified variant of the plasmid pHD313 (Dalböge et al., 1989). The vector which was replicated in E. coli (contains origin of replication from plasmid pUC19) is constructed such that DNA-fragments which have been cloned in the cleaving site for NarI will be expressed immediately after, or downstream, of the signal peptide (21 amino acids) from the envelope protein ompA from E. coli. Translation will be initiated from the ATG-codon which codes for the first amino acid (methionine) in the signal peptide. The construction with an E. coli-individual signal sequence which precedes the desired peptide enables the translated peptide to be transported to the periplasmic space in E. coli. This is beneficial since it reduces the risk of degradation of the desired product through the intracellular occurrent enzymes of E. coli. Furthermore, it is easier to purify peptides which have been exported to the periplasmatic space. Unique recognition sequences (multiple cloning sequences) for several other restriction enzymes, among them EcoRI, SalI and BamHI are present immediately downstream of the NarI cleaving site. An optimized so-called Shine-Dalgarno sequence (also called ribosomal binding site, RBS) is found seven nucleotides upstream of the ATG-codon in the signal sequence from ompA, this optimized Shine-Dalgarno sequence binding to a complementary sequence in 16S rRNA in the ribosomes and in a manner to decide that the translation is initiated in the correct place. The transcription of such DNA as that which is co-transcribed with the signal sequence for ompA is controlled by the $P_R$-promotor from coliphage λ. The vector also contains the gene for cI857 from coliphage λ, the product of which regulates-down transcription from $P_R$ and the product of which is expressed constitutively. This cI857-mediated down-regulation of transcription from $P_R$ is heat-sensitive. Transcription which is regulated, or controlled, from this promotor will be terminated with the aid of a so-called rho-independent transcription terminating sequence which is inserted in the vector immediately downstream of the multiple cloning site. The plasmid also carries the gene for β-lactamase (from the plasmid pUC19), the product of which permits ampicillin-selection of E. coli clones that have been transformed with the vector.

Selection of Protein LG-Produced Clones

The transformed bacteria are cultivated on culture plates with LB-medium which also contained ampicillin in a concentration of 100 µg/ml. The bacteria were cultivated overnight at 30° C., whereafter they were transferred to a cultivation cabinet (42° C.) and cultured for a further four (4) hours. The plates were stored in a refrigerator overnight. On the following day, the colonies were transferred to nitrocellulose filters. The filters and culture plates were marked, so that the transferred colonies could later be identified on the culture plate. The culture plates were again incubated overnight at 30° C., so that rests of transferred bacteria colonies remaining on the plates could again grow. The plates were then stored in a refrigerator. The filter was incubated in 10% SDS for 10 minutes, so as to lyse the bacteria in the colonies on the nitrocellulose impression. Filters containing lysed bacteria were then rinsed with a blocking buffer consisting of PBS (pH 7.2) with 0.25% gelatine and 0.25% Tween-20 (four baths of 250 ml at 37° C.), whereafter the filter was incubated with radioactively (marked with $^{125}$I according to the chloromine-T-method) marked Ig-κ-chains (20 ng/ml) in PBS with 0.1% gelatine). The incubation process took place at room temperature for four (4) hours, whereafter non-bound radioactively marked protein was rinsed-off with PBS (pH 7.2) containing 0.5 M NaCl, 0.25% gelatine and 0.25% Tween-20 (four baths, 250 ml each at room temperature). All filters were exposed to X-ray film. Positive colonies on the original culture plate were identified. A number of positive colonies were re-cultivated on new plates and new colony-blot experiments were carried out with these plates as a starting material with the intention of identifying E. coli colonies which bind IgG Fc. These tests were carried out in precisely the same manner as that described above with respect to the identification of E. coli-colonies which expressed Ig light-chain-binding protein, with the exception that a radioactively marked ($^{125}$I) IgG Fc (20 ng/ml) was used as a probe. Clones which reacted with both proteins were selected and analyzed with regard to the size of the DNA-fragment introduced in the vector. One of these clones was chosen for production of protein LG, pHDLG. The DNA taken from this clone and introduced into plasmid pHD389 was sequenced. The DNA-sequence exhibited full agreement with corresponding sequences (B1–B4 and 21 bases in B5) in the gene for protein L from Peptostreptococcus magnus, strain 312, and with C1 DC2 sequence in group C streptococcus strain C40. The size and binding properties of the protein produced from clone pHDLG was analyzed with the aid of SDS-PAGE (see FIG. 8), dot-blot experiment (see FIG. 10) and competitive binding experiments.

Production of Protein LG

Several colonies from a culture plate with E. coli pHDLG were used to inoculate a preculture (LB-medium with an addition of 100 mg/l ampicillin) were cultivated at 28° C. overnight. In the morning, the preculture was transferred to a larger volume (100 times the volume of the preculture) of fresh LB-medium containing ampicillin (100 mg/l) and was cultivated in vibrating flasks (200 rpm), (or fermenters) at 28° C. When an absorbence value of 0.5 was reached at 620 nm, the cultivation temperature was raised to 40° C. (induction of transcription). The cultivation process was then continued for 4 hours (applies only to cultivation in vibrated flasks). The bacteria were centrifuged down upon termination of the cultivation process. The bacteria were then lysed at 4° C. in accordance with an osmotic shock method (Dalböge et al., 1989). The lysate was adjusted to a pH of 7. Remaining bacteria rests were centrifuged down and the supernatent then purified on IgG-sepharose, in accordance with the protocol earlier described with reference to protein G and protein L. (Sjöbring et al., 1991, Kastern et al., 1992).

The expression system gave about 30 mg/l of protein LG when cultivation in vibrated flasks. A deposition has been made at DSSM, Identification Reference DSSM E. coli LE392/pHDLG.

EXAMPLE 3
Analysis of the Binding Properties of Protein LG
Western Blot Protein G (the C1DC2-fragment), protein L (four B-domains) and protein LG were isolated with SDS-PAGE (10% acrylamide concentration). The isolated proteins were transferred to nitrocellulose membranes in three similar copies (triplicate). Each of these membranes was incubated with radioactively marked proteins (20 ng/ml: one of the membrane-copies was incubated with human polyclonal IgG, another with human IgG Fc-fragment and the third with isolated human IgG χchains. Non-bound radioactively marked proteins were rinsed off and all filters were then exposed to X-ray film.

Slot-Blot

Human polyclonal Ig-preparations and Ig-fragments were applied with the aid of a slot-blot appliances on nitrocellulose filters in given quantities (see FIG. 10) on three similar copies. Each of these membranes was incubated with radioactively marked proteins (20 ng/ml). One of the membrane copies was incubated with protein LG, another with protein L and the third with protein G. Non-bound radioactively marked proteins were rinsed-off and all filters were then exposed to X-ray film.

Figure 9:
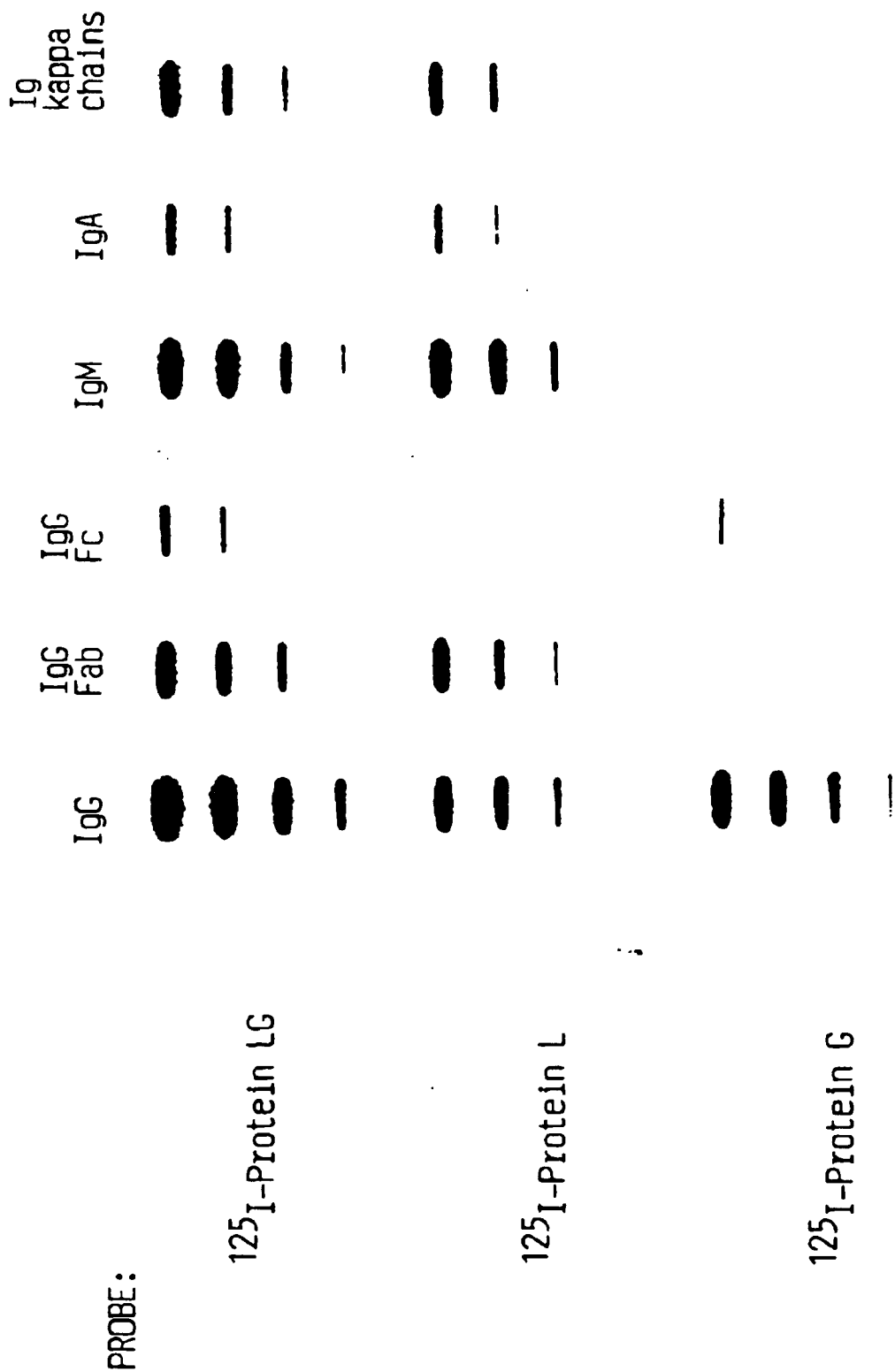
FIG. 9 illustrates Slot-Blot for protein L, G and LG with IgG, Igχ and Ig Fc.

The results are shown in FIGS. 9 and 10.

Other binding experiments have been carried out, with the following results:

TABLE

Binding of the proteins G, L and LG to immunoglobulins.

| Immunoglobulin | G | $K_a$ | L | $K_a$ | LG | $K_a$ |
|---|---|---|---|---|---|---|
| Human: | | | | | | |
| Polyclonal IgG* | + | 67(10) | + | 9.0 | + | 20 |
| IgG subclasses | | | | | | |
| IgG$_1$ | + | 2.0 | + | | + | |
| IgG$_2$ | + | 3.1 | + | | + | |
| IgG$_3$ | + | 6.1 | + | | + | |
| IgG$_4$ | + | 4.7 | + | | + | |
| IgG fragment | | | | | | |
| Fc* | + | 6.0(0.5) | − | | + | |
| F(ab')$_2$* | + | 0.4(0.2) | + | | + | |
| kappa | − | | + | | + | 1.5 |
| lambda | − | | (−)# | | | |
| Other Ig-classes | | | | | | |
| IgM | − | | + | 11.6 | + | |
| IgA | − | | + | 10.4 | + | |
| IgE | − | | + | | + | |
| IgD | − | | | | | |
| Other Species: | | | | | | |
| Polyclonal | | | | | | |
| Monkey | + | | + | | + | |
| Rabbit IgG | + | 70 | + | 0.074 | + | |
| IgG-Fc | + | 3.0 | − | | + | |
| IgG-F(ab')$_2$ | + | 0.44 | + | | + | |
| Mouse | + | 41 | + | 2.6 | + | |
| Rat | + | 1.5 | + | 0.39 | + | |
| Goat | + | 14 | − | | + | |
| Bovine | | | | | | |
| IgG$_1$ | + | 3 | − | | + | |
| IgG$_2$ | + | 2 | − | | + | |
| Horse | + | | − | | + | |
| Guinea Pig | + | | + | | + | |
| Sheep | + | | − | | + | |
| Dog | + | | − | | + | |
| Pig | + | | + | | + | |
| Hamster | + | | | | | |
| Cat | − | | − | | | |
| Hen | − | | − | | | |
| Monclonals& | | | | | | |
| Mouse | | | | | | |
| IgG$_1$ | + | | + | | + | |
| IgG$_{2a}$ | + | | + | | + | |
| IgG$_{2b}$ | + | | | | + | |
| IgG$_3$ | + | | | | + | |
| IgM | − | | + | | + | |
| IgA | − | | + | | + | |
| Rat | | | | | | |
| IgG$_{2a}$ | + | | + | | + | |
| IgG$_{2b}$ | + | | | | + | |
| IgG$_{2c}$ | + | | | | + | |

$K_a$ = affinity constant (M$^{-1}$).
*The numerals within parenthesis disclose the affinity of a recumbinant protein G comprised of two IgG-binding domains.
A weak bond to lambda chains exists. Binding to P1 and PLG depends on the type of light chain of Ig.

It will thus be seen that the synthesized hybrid protein LG has a broad binding activity/specificity.

---

What is claimed is:

1. An isolated protein having the ability to bind to the light chains of immunoglobulins, wherein said protein is selected from the group consisting of:
   (a) a protein consisting essentially of the amino acid sequence of SEQ ID NO: 1;
   (b) a protein consisting essentially of the amino acid sequence of at least one of the domains B1, B2, B3 or B4 of (a) wherein,
      (i) domain B1 is comprised of from amino acid 5 to amino acid 80 of SEQ ID NO: 1;
      (ii) domain B2 is comprised of from amino acid 81 to amino acid 152 of SEQ ID NO: 1;
      (iii) domain B3 is comprised of from amino acid 153 to amino acid 224 of SEQ ID NO: 1;
      (iv) domain B4 is comprised of from amino acid 225 to amino acid 296 of SEQ ID NO: 1; and
   (c) a protein consisting essentially of the sequence of multiple domains selected from one or more of the domains B1, B2, B3 and B4 of (b).

2. An isolated hybrid protein consisting essentially of one or more of the B1–B4 domains according to claim 1 which bind to the light chains in immunoglobulins of all classes, and domains which bind to heavy chains of immunoglobulin G.

3. A hybrid protein according to claim 2, wherein the domains which bind to heavy chains of immunoglobulin G are chosen from among:
   (i) the C1- and C2-domains in protein G, wherein domain C1 is comprised of from amino acid 303 to amino acid 357 of protein G and domain C2 is comprised of from amino acid 373 to amino acid 427 of protein G;
   (ii) the A-, B- and C1-domains in protein H wherein domain A is comprised of from amino acid 42 to amino acid 121 of protein H, domain B is comprised of from amino acid 122 to amino acid 158 of protein H, and domain C1 is comprised of from amino acid 159 to amino acid 200 of protein H;
   (iii) the A-, B1-, B2- and S domains in protein M1, wherein domain A is comprised of from amino acid 1 to amino acid 91 of protein M1, domain B1- is comprised of from amino acid 92 to amino acid 119 of protein M1, domain B2- is comprised of from amino acid 120 to amino acid 147 of protein M1, and domain S is comprised of from amino acid 154 to amino acid 190 of protein M1; or
   (iv) the E-, D-, A-, B- and C- domains in protein A, wherein domain E- is comprised of from amino acid 37 to amino acid 92 of protein A, domain D- is comprised of from amino acid 93 to amino 153 of protein A, domain A- is comprised of from amino acid 154 to amino acid 211 of protein A, domain B- is comprised of from amino acid 212 to amino acid 269 of protein A, and domain C- is comprised of from amino acid 270 to amino acid 327 of protein A.

4. A hybrid protein according to claim 3, wherein the hybrid protein has the amino acid sequence of SEQ ID NO: 3.

5. A reagent kit for binding, separating and identifying immunoglobulins, comprising a protein according to any one of claim 1, 2, 3 or 4, and a detection reagent.

6. A composition, comprising a protein according to any one of claim 1, 2, 3 or 4 in combination with an additive or carrier.

7. An isolated hybrid protein consisting essentially of the amino acid sequence of SEQ ID NO: 3.

* * * * *

SEQUENCE LISTING (1) GENERAL INFORMATION:

(iii) NUMBER OF SEQUENCES: 15

(2) INFORMATION FOR SEQ ID NO: 1:

(i) SEQUENCE CHARACTERISTICS:
      (A) LENGTH: 305 amino acids
      (B) TYPE: amino acid
      (C) STRANDEDNESS: unknown
      (D) TOPOLOGY: unknown (ii) MOLECULE TYPE: protein (iii) HYPOTHETICAL: NO (vi) ORIGINAL SOURCE:
   (A) ORGANISM: Escherichia coli LE392/pHDL, DSM 7054

(xi) SEQUENCE DESCRIPTION: SEQ ID NO: 1:

```
Ala Val Glu Asn Lys Glu Thr Pro Glu Thr Pro Glu Thr Asp Se
1               5                   10                  15

Glu Glu Glu Val Thr Ile Lys Ala Asn Leu Ile Phe Ala Asn Gly Se
                20                  25                  30

Thr Gln Thr Ala Glu Phe Lys Gly Thr Phe Glu Lys Ala Thr Ser Gl
            35                  40                  45

Ala Tyr Ala Tyr Ala Asp Thr Leu Lys Lys Asp Asn Gly Glu Tyr Th
50                      55                  60

Val Asp Val Ala Asp Lys Gly Tyr Thr Leu Asn Ile Lys Phe Ala Gl
65                  70                  75                  80

Lys Glu Lys Thr Pro Glu Glu Pro Lys Glu Glu Val Thr Ile Lys Al
                85                  90                  95

Asn Leu Ile Tyr Ala Asp Gly Lys Thr Gln Thr Ala Glu Phe Lys Gl
                100                 105                 110

Thr Phe Glu Glu Ala Thr Ala Glu Ala Tyr Arg Tyr Ala Asp Ala Le
            115                 120                 125

Lys Lys Asp Asn Gly Glu Tyr Thr Val Asp Val Ala Asp Lys Gly Ty
    130                 135                 140

Thr Leu Asn Ile Lys Phe Ala Gly Lys Glu Lys Thr Pro Glu Glu Pr
145                 150                 155                 160

Lys Glu Glu Val Thr Ile Lys Ala Asn Leu Ile Tyr Ala Asp Gly Ly
                165                 170                 175

Thr Gln Thr Ala Glu Phe Lys Gly Thr Phe Glu Glu Ala Thr Ala Gl
            180                 185                 190

Ala Tyr Arg Tyr Ala Asp Leu Leu Ala Lys Glu Asn Gly Lys Tyr Th
    195                 200                 205

Val Asp Val Ala Asp Lys Gly Tyr Thr Leu Asn Ile Lys Phe Ala Gl
210                 215                 220

Lys Glu Lys Thr Pro Glu Glu Pro Lys Glu Glu Val Thr Ile Lys Al
225                 230                 235                 240

Asn Leu Ile Tyr Ala Asp Gly Lys Thr Gln Thr Ala Glu Phe Lys Gl
                245                 250                 255

Thr Phe Ala Glu Ala Thr Ala Glu Ala Tyr Arg Tyr Ala Asp Leu Le
            260                 265                 270

Ala Lys Glu Asn Gly Lys Tyr Thr Ala Asp Leu Glu Asp Gly Gly Ty
    275                 280                 285

Thr Ile Asn Ile Arg Phe Ala Gly Lys Lys Val Asp Glu Lys Pro Gl
    290                 295                 300

Glu
305
```

(2) INFORMATION FOR SEQ ID NO: 2:

(i) SEQUENCE CHARACTERISTICS:
       (A) LENGTH: 921 base pairs
       (B) TYPE: nucleic acid
       (C) STRANDEDNESS: double
       (D) TOPOLOGY: unknown (ii) MOLECULE TYPE: DNA (genomic)

(iii) HYPOTHETICAL: NO (vi) ORIGINAL SOURCE:
             (A) ORGANISM: Escherichia coli LE392/pHDL, DSM 7054

(xi) SEQUENCE DESCRIPTION: SEQ ID NO: 2:

GCGGTAGAAA ATAAAGAAGA AACACCAGAA ACACCAGAAA CTGATTCAGA AGAAGAAGTA    60

ACAATCAAAG CTAACCTAAT CTTTGCAAAT GGAAGCACAC AAACTGCAGA ATTCAAAGG    120

ACATTTGAAA AAGCAACATC AGAAGCTTAT GCGTATGCAG ATACTTTGAA GAAAGACAA    180

GGAGAATATA CTGTAGATGT TGCAGATAAA GGTTATACTT TAAATATTAA ATTTGCTGG    240

AAAGAAAAAA CACCAGAAGA ACCAAAGAA GAAGTTACTA TTAAAGCAAA CTTAATCTA    300

GCAGATGGAA AAACACAAAC AGCAGAATTC AAAGGAACAT TTGAAGAAGC AACAGCAGA    360

GCATACAGAT ATGCAGATGC ATTAAAGAAG GACAATGGAA AATATACAGT AGACGTTGC    420

GATAAAGGTT ATACTTTAAA TATTAAATTT GCTGGAAAAG AAAAAACACC AGAAGAACC    480

AAAGAAGAAG TTACTATTAA AGCAAACTTA ATCTATGCAG ATGGAAAAAC ACAAACAGC    540

GAATTCAAAG GAACATTTGA AGAAGCAACA GCAGAAGCAT ACAGATATGC TGACTTATT    600

GCAAAAGAAA ATGGTAAATA TACAGTAGAC GTTGCAGATA AAGGTTATAC TTTAAATAT    660

AAATTTGCTG GAAAAGAAAA AACACCAGAA GAACCAAAAG AAGAAGTTAC TATTAAAGC    720

AACTTAATCT ATGCAGATGG AAAAACTCAA ACAGCAGAGT TCAAAGGAAC ATTTGCAGA    780

GCAACAGCAG AAGCATACAG ATACGCTGAC TTATTAGCAA AAGAAAATGG TAAATATAC    840

GCAGACTTAG AAGATGGTGG ATACACTATT AATATTAGAT TTGCAGGTAA GAAAGTTGA    900

GAAAAACCAG AAGAATAATA A                                             921

(2) INFORMATION FOR SEQ ID NO: 3:

(i) SEQUENCE CHARACTERISTICS:
        (A) LENGTH: 434 amino acids
        (B) TYPE: amino acid
        (C) STRANDEDNESS: unknown
        (D) TOPOLOGY: unknown (ii) MOLECULE TYPE: protein (iii) HYPOTHETICAL: NO (vi) ORIGINAL SOURCE:
         (A) ORGANISM: Escherichia coli LE392/pHDLG, DSM 7055

(xi) SEQUENCE DESCRIPTION: SEQ ID NO: 3:

Ala Val Glu Asn Lys Glu Glu Thr Pro Glu Thr Pro Glu Thr Asp Se
1               5                   10                  15

Glu Glu Glu Val Thr Ile Lys Ala Asn Leu Ile Phe Ala Asn Gly Se
            20                  25                  30

Thr Gln Thr Ala Glu Phe Lys Gly Thr Phe Glu Lys Ala Thr Ser Gl
        35                  40                  45

Ala Tyr Ala Tyr Ala Asp Thr Leu Lys Lys Asp Asn Gly Glu Tyr Th
    50                  55                  60

Val Asp Val Ala Asp Lys Gly Tyr Thr Leu Asn Ile Lys Phe Ala Gl
65                  70                  75                  80

Lys Glu Lys Thr Pro Glu Glu Pro Lys Glu Glu Val Thr Ile Lys Al
                85                  90                  95

Asn Leu Ile Tyr Ala Asp Gly Lys Thr Gln Thr Ala Glu Phe Lys Gl
            100                 105                 110

Thr Phe Glu Glu Ala Thr Ala Glu Ala Tyr Arg Tyr Ala Asp Ala Le
        115                 120                 125

```
Lys Lys Asp Asn Gly Glu Tyr Thr Val Asp Val Ala Asp Lys Gly Ty
    130                 135                 140
Thr Leu Asn Ile Lys Phe Ala Gly Lys Glu Lys Thr Pro Glu Glu Pr
145                 150                 155                 160
Lys Glu Glu Val Thr Ile Lys Ala Asn Leu Ile Tyr Ala Asp Gly Ly
                165                 170                 175
Thr Gln Thr Ala Glu Phe Lys Gly Thr Phe Glu Glu Ala Thr Ala Gl
            180                 185                 190
Ala Tyr Arg Tyr Ala Asp Leu Leu Ala Lys Glu Asn Gly Lys Tyr Th
        195                 200                 205
Val Asp Val Ala Asp Lys Gly Tyr Thr Leu Asn Ile Lys Phe Ala Gl
    210                 215                 220
Lys Glu Lys Thr Pro Glu Glu Pro Lys Glu Glu Val Thr Ile Lys Al
225                 230                 235                 240
Asn Leu Ile Tyr Ala Asp Gly Lys Thr Gln Thr Ala Glu Phe Lys Gl
                245                 250                 255
Thr Phe Ala Glu Ala Thr Ala Glu Ala Tyr Arg Tyr Ala Asp Leu Le
            260                 265                 270
Ala Lys Glu Asn Gly Lys Tyr Thr Ala Asp Leu Glu Asp Gly Gly Ty
        275                 280                 285
Thr Ile Asn Ile Arg Phe Ala Gly Lys Lys Val Asp Glu Lys Pro Gl
    290                 295                 300
Glu Pro Met Asp Thr Tyr Lys Leu Ile Leu Asn Gly Lys Thr Leu Ly
305                 310                 315                 320
Gly Glu Thr Thr Thr Glu Ala Val Asp Ala Ala Thr Ala Glu Lys Va
                325                 330                 335
Phe Lys Gln Tyr Ala Asn Asp Asn Gly Val Asp Gly Glu Trp Thr Ty
            340                 345                 350
Asp Asp Ala Thr Lys Thr Phe Thr Val Thr Glu Lys Pro Glu Val Il
        355                 360                 365
Asp Ala Ser Glu Leu Thr Pro Ala Val Thr Thr Tyr Lys Leu Val Il
    370                 375                 380
Asn Gly Lys Thr Leu Lys Gly Glu Thr Thr Thr Lys Ala Val Asp Al
385                 390                 395                 400
Glu Thr Ala Glu Lys Ala Phe Lys Gln Tyr Ala Asn Asp Asn Gly Va
                405                 410                 415
Asp Gly Val Trp Thr Tyr Asp Asp Ala Thr Lys Thr Phe Thr Val Th
            420                 425                 430
Glu Met
```

(2) INFORMATION FOR SEQ ID NO: 4:

(i) SEQUENCE CHARACTERISTICS:
        (A) LENGTH: 1308 base pairs
        (B) TYPE: nucleic acid
        (C) STRANDEDNESS: double
        (D) TOPOLOGY: unknown (ii) MOLECULE TYPE: DNA (genomic)

(iii) HYPOTHETICAL: NO (vi) ORIGINAL SOURCE:
        (A) ORGANISM: Escherichia coli L392/pHDLG, DSM 7055

(xi) SEQUENCE DESCRIPTION: SEQ ID NO: 4:

```
GCGGTAGAAA ATAAAGAAGA AACACCAGAA ACACCAGAAA CTGATTCAGA AGAAGAAGTA    60
```

```
ACAATCAAAG CTAACCTAAT CTTTGCAAAT GGAAGCACAC AAACTGCAGA ATTCAAAGG      120

ACATTTGAAA AAGCAACATC AGAAGCTTAT GCGTATGCAG ATACTTTGAA GAAAGACAA      180

GGAGAATATA CTGTAGATGT TGCAGATAAA GGTTATACTT TAAATATTAA ATTTGCTGG      240

AAAGAAAAAA CACCAGAAGA ACCAAAAGAA GAAGTTACTA TTAAAGCAAA CTTAATCTA      300

GCAGATGGAA AACACAAAC AGCAGAATTC AAAGGAACAT TGAAGAAGC AACAGCAGA        360

GCATACAGAT ATGCAGATGC ATTAAAGAAG GACAATGGAG AATATACAGT AGACGTTGC      420

GATAAAGGTT ATACTTTAAA TATTAAATTT GCTGGAAAAG AAAAAACACC AGAAGAACC     480

AAAGAAGAAG TTACTATTAA AGCAAACTTA ATCTATGCAG ATGGAAAAAC ACAAACAGC     540

GAATTCAAAG GAACATTTGA AGAAGCAACA GCAGAAGCAT ACAGATATGC TGACTTATT     600

GCAAAAGAAA ATGGTAAATA TACAGTAGAC GTTGCAGATA AAGGTTATAC TTTAAATAT     660

AAATTTGCTG GAAAGAAAAA AACACCAGAA GAACCAAAAG AAGAAGTTAC TATTAAAGC     720

AACTTAATCT ATGCAGATGG AAAAACTCAA ACAGCAGAGT TCAAAGGAAC ATTTGCAGA     780

GCAACAGCAG AAGCATACAG ATACGCTGAC TTATTAGCAA AAGAAAATGG TAAATATAC     840

GCAGACTTAG AAGATGGTGG ATACACTATT AATATTAGAT TTGCAGGTAA GAAAGTTGA     900

GAAAAACCAG AAGAACCCAT GGACACTTAC AAATTAATCC TTAATGGTAA AACATTGAA     960

GGCGAAACAA CTACTGAAGC TGTTGATGCT GCTACTGCAG AAAAAGTCTT CAAACAAT    1020

GCTAACGACA ACGGTGTTGA CGGTGAATGG ACTTACGACG ATGCGACTAA GACCTTTA    1080

GTTACTGAAA AACCAGAAGT GATCGATGCG TCTGAATTAA CACCAGCCGT GACAACTT    1140

AAACTTGTTA TTAATGGTAA ACATTGAAA GGCGAAACAA CTACTAAAGC AGTAGACG    1200

GAAACTGCAG AAAAAGCCTT CAAACAATAC GCTAACGACA ACGGTGTTGA TGGTGTTT    1260

ACTTATGATG ATGCGACTAA GACCTTTACG GTAACTGAAA TGTAATAA              1308
```

(2) INFORMATION FOR SEQ ID NO: 5:

(i) SEQUENCE CHARACTERISTICS:
        (A) LENGTH: 1332 base pairs
        (B) TYPE: nucleic acid
        (C) STRANDEDNESS: double
        (D) TOPOLOGY: unknown (ii) MOLECULE TYPE: DNA (genomic)

(iii) HYPOTHETICAL: NO (ix) FEATURE:
        (A) NAME/KEY: CDS
        (B) LOCATION: 1..1329

(xi) SEQUENCE DESCRIPTION: SEQ ID NO: 5:

```
AAC GGT GAT GGT AAT CCT AGG GAA GTT ATA GAA GAT CTT GCA GCA AAC         48
Asn Gly Asp Gly Asn Pro Arg Glu Val Ile Glu Asp Leu Ala Ala Asn
 1               5                  10                  15

AAT CCC GCA ATA CAA AAT ATA CGT TTA CGT CAC GAA AAC AAG GAC TTA         96
Asn Pro Ala Ile Gln Asn Ile Arg Leu Arg His Glu Asn Lys Asp Leu
                20                  25                  30

AAA GCG AGA TTA GAG AAT GCA ATG GAA GTT GCA GGA AGA GAT TTT AAG        144
Lys Ala Arg Leu Glu Asn Ala Met Glu Val Ala Gly Arg Asp Phe Lys
            35                  40                  45

AGA GCT GAA GAA CTT GAA AAA GCA AAA CAA GCC TTA GAA GAC CAG CGT        192
Arg Ala Glu Glu Leu Glu Lys Ala Lys Gln Ala Leu Glu Asp Gln Arg
        50                  55                  60

AAA GAT TTA GAA ACT AAA TTA AAA GAA CTA CAA CAA GAC TAT GAC TTA        240
```

```
                                                                -continued

Lys Asp Leu Glu Thr Lys Leu Lys Glu Leu Gln Gln Asp Tyr Asp Leu
 65                  70                  75                  80

GCA AAG GAA TCA ACA AGT TGG GAT AGA CAA AGA CTT GAA AAA GAG TTA     288
Ala Lys Glu Ser Thr Ser Trp Asp Arg Gln Arg Leu Glu Lys Glu Leu
                     85                  90                  95

GAA GAG AAA AAG GAA GCT CTT GAA TTA GCG ATA GAC CAG GCA AGT CGG     336
Glu Glu Lys Lys Glu Ala Leu Glu Leu Ala Ile Asp Gln Ala Ser Arg
                100                 105                 110

GAC TAC CAT AGA GCT ACC GCT TTA GAA AAA GAG TTA GAA GAG AAA AAG     384
Asp Tyr His Arg Ala Thr Ala Leu Glu Lys Glu Leu Glu Glu Lys Lys
            115                 120                 125

AAA GCT CTT GAA TTA GCG ATA GAC CAA GCG AGT CAG GAC TAT AAT AGA     432
Lys Ala Leu Glu Leu Ala Ile Asp Gln Ala Ser Gln Asp Tyr Asn Arg
    130                 135                 140

GCT AAC GTC TTA GAA AAA GAG TTA GAA ACG ATT ACT AGA GAA CAA GAG     480
Ala Asn Val Leu Glu Lys Glu Leu Glu Thr Ile Thr Arg Glu Gln Glu
145                 150                 155                 160

ATT AAT CGT AAT CTT TTA GGC AAT GCA AAA CTT GAA CTT GAT CAA CTT     528
Ile Asn Arg Asn Leu Leu Gly Asn Ala Lys Leu Glu Leu Asp Gln Leu
                165                 170                 175

TCA TCT GAA AAA GAG CAG CTA ACG ATC GAA AAA GCA AAA CTT GAG GAA     576
Ser Ser Glu Lys Glu Gln Leu Thr Ile Glu Lys Ala Lys Leu Glu Glu
                180                 185                 190

GAA AAA CAA ATC TCA GAC GCA AGT CGT CAA AGC CTT CGT CGT GAC TTG     624
Glu Lys Gln Ile Ser Asp Ala Ser Arg Gln Ser Leu Arg Arg Asp Leu
                195                 200                 205

GAC GCA TCA CGT GAA GCT AAG AAA CAG GTT GAA AAA GAT TTA GCA AAC     672
Asp Ala Ser Arg Glu Ala Lys Lys Gln Val Glu Lys Asp Leu Ala Asn
210                 215                 220

TTG ACT GCT GAA CTT GAT AAG GTT AAA GAA GAC AAA CAA ATC TCA GAC     720
Leu Thr Ala Glu Leu Asp Lys Val Lys Glu Asp Lys Gln Ile Ser Asp
225                 230                 235                 240

GCA AGC CGT CAA CGG CTT CGC CGT GAC TTG GAC GCA TCA CGT GAA GCT     768
Ala Ser Arg Gln Arg Leu Arg Arg Asp Leu Asp Ala Ser Arg Glu Ala
                245                 250                 255

AAG AAA CAG GTT GAA AAA GAT TTA GCA AAC TTG ACT GCT GAA CTT GAT     816
Lys Lys Gln Val Glu Lys Asp Leu Ala Asn Leu Thr Ala Glu Leu Asp
                260                 265                 270

AAG GTT AAA GAA GAA AAA CAA ATC TCA GAC GCA AGC CGT CAA CGG CTT     864
Lys Val Lys Glu Glu Lys Gln Ile Ser Asp Ala Ser Arg Gln Arg Leu
                275                 280                 285

CGC CGT GAC TTG GAC GCA TCA CGT GAA GCT AAG AAA CAA GTT GAA AAA     912
Arg Arg Asp Leu Asp Ala Ser Arg Glu Ala Lys Lys Gln Val Glu Lys
                290                 295                 300

GCT TTA GAA GAA GCA AAC AGC AAA TTA GCT GCT CTT GAA AAA CTT AAC     960
Ala Leu Glu Glu Ala Asn Ser Lys Leu Ala Ala Leu Glu Lys Leu Asn
305                 310                 315                 320

AAA GAG CTT GAA GAA AGC AAG AAA TTA ACA GAA AAA GAA AAA GCT GAA    1008
Lys Glu Leu Glu Glu Ser Lys Lys Leu Thr Glu Lys Glu Lys Ala Glu
                325                 330                 335

CTA CAA GCA AAA CTT GAA GCA GAA GCA AAA GCA CTC AAA GAA CAA TTA    1056
Leu Gln Ala Lys Leu Glu Ala Glu Ala Lys Ala Leu Lys Glu Gln Leu
                340                 345                 350

GCG AAA CAA GCT GAA GAA CTC GCA AAA CTA AGA GCT GGA AAA GCA TCA    1104
Ala Lys Gln Ala Glu Glu Leu Ala Lys Leu Arg Ala Gly Lys Ala Ser
                355                 360                 365

GAC TCA CAA ACC CCT GAT ACA AAA CCA GGA AAC AAA GCT CTT CCA GGT    1152
Asp Ser Gln Thr Pro Asp Thr Lys Pro Gly Asn Lys Val Leu Pro Gly
370                 375                 380
```

```
AAA GGT CAA GCA CCA CAA GCA GGT ACA AAA CCT AAC CAA AAC AAA GCA          1200
Lys Gly Gln Ala Pro Gln Ala Gly Thr Lys Pro Asn Gln Asn Lys Ala
385                 390                 395                 400

CCA ATG AAG GAA ACT AAG AGA CAG TTA CCA TCA ACA GGT GAA ACA GCT          1248
Pro Met Lys Glu Thr Lys Arg Gln Leu Pro Ser Thr Gly Glu Thr Ala
                405                 410                 415

AAC CCA TTC TTC ACA GCG GCA CGC GTT ACT GTT ATG GCA ACA GCT GGA          1296
Asn Pro Phe Phe Thr Ala Ala Arg Val Thr Val Met Ala Thr Ala Gly
            420                 425                 430

GTA GCA GCA GTT GTA AAA CGC AAA GAA GAA AAC TAA                          1332
Val Ala Ala Val Val Lys Arg Lys Glu Glu Asn
        435                 440
```

(2) INFORMATION FOR SEQ ID NO: 6:

(i) SEQUENCE CHARACTERISTICS:
        (A) LENGTH: 443 amino acids
        (B) TYPE: amino acid
        (D) TOPOLOGY: linear (ii) MOLECULE TYPE: protein (xi) SEQUENCE DESCRIPTION: SEQ ID NO: 6:

```
Asn Gly Asp Gly Asn Pro Arg Glu Val Ile Glu Asp Leu Ala Ala Asn
  1               5                  10                  15

Asn Pro Ala Ile Gln Asn Ile Arg Leu Arg His Glu Asn Lys Asp Leu
                20                  25                  30

Lys Ala Arg Leu Glu Asn Ala Met Glu Val Ala Gly Arg Asp Phe Lys
            35                  40                  45

Arg Ala Glu Glu Leu Glu Lys Ala Lys Gln Ala Leu Glu Asp Gln Arg
 50                  55                  60

Lys Asp Leu Glu Thr Lys Leu Lys Glu Leu Gln Gln Asp Tyr Asp Leu
 65                  70                  75                  80

Ala Lys Glu Ser Thr Ser Trp Asp Arg Gln Arg Leu Glu Lys Glu Leu
                85                  90                  95

Glu Glu Lys Lys Glu Ala Leu Glu Leu Ala Ile Asp Gln Ala Ser Arg
                100                 105                 110

Asp Tyr His Arg Ala Thr Ala Leu Glu Lys Glu Leu Glu Glu Lys Lys
            115                 120                 125

Lys Ala Leu Glu Leu Ala Ile Asp Gln Ala Ser Gln Asp Tyr Asn Arg
130                 135                 140

Ala Asn Val Leu Glu Lys Glu Leu Glu Thr Ile Thr Arg Glu Gln Glu
145                 150                 155                 160

Ile Asn Arg Asn Leu Leu Gly Asn Ala Lys Leu Glu Leu Asp Gln Leu
                165                 170                 175

Ser Ser Glu Lys Glu Gln Leu Thr Ile Glu Lys Ala Lys Leu Glu Glu
                180                 185                 190

Glu Lys Gln Ile Ser Asp Ala Ser Arg Gln Ser Leu Arg Arg Asp Leu
            195                 200                 205

Asp Ala Ser Arg Glu Ala Lys Lys Gln Val Glu Lys Asp Leu Ala Asn
210                 215                 220

Leu Thr Ala Glu Leu Asp Lys Val Lys Glu Asp Lys Gln Ile Ser Asp
225                 230                 235                 240

Ala Ser Arg Gln Arg Leu Arg Arg Asp Leu Asp Ala Ser Arg Glu Ala
                245                 250                 255

Lys Lys Gln Val Glu Lys Asp Leu Ala Asn Leu Thr Ala Glu Leu Asp
                260                 265                 270
```

```
Lys Val Lys Glu Glu Lys Gln Ile Ser Asp Ala Ser Arg Gln Arg Leu
        275                 280                 285

Arg Arg Asp Leu Asp Ala Ser Arg Glu Ala Lys Lys Gln Val Glu Lys
        290                 295                 300

Ala Leu Glu Glu Ala Asn Ser Lys Leu Ala Ala Leu Glu Lys Leu Asn
305                 310                 315                 320

Lys Glu Leu Glu Glu Ser Lys Lys Leu Thr Glu Lys Glu Lys Ala Glu
                325                 330                 335

Leu Gln Ala Lys Leu Glu Ala Glu Ala Lys Ala Leu Lys Glu Gln Leu
                340                 345                 350

Ala Lys Gln Ala Glu Glu Leu Ala Lys Leu Arg Ala Gly Lys Ala Ser
        355                 360                 365

Asp Ser Gln Thr Pro Asp Thr Lys Pro Gly Asn Lys Ala Val Pro Gly
        370                 375                 380

Lys Gly Gln Ala Pro Gln Ala Gly Thr Lys Pro Asn Gln Asn Lys Ala
385                 390                 395                 400

Pro Met Lys Glu Thr Lys Arg Gln Leu Pro Ser Thr Gly Glu Thr Ala
                405                 410                 415

Asn Pro Phe Phe Thr Ala Ala Arg Val Thr Val Met Ala Thr Ala Gly
                420                 425                 430

Val Ala Ala Val Val Lys Arg Lys Glu Glu Asn
        435                 440

(2) INFORMATION FOR SEQ ID NO: 7:

(i) SEQUENCE CHARACTERISTICS:
        (A) LENGTH: 44 base pairs
        (B) TYPE: nucleic acid
        (C) STRANDEDNESS: single
        (D) TOPOLOGY: linear (xi) SEQUENCE DESCRIPTION: SEQ ID NO: 7:

GCTCAGGCGG CGCCGGTAGA AAATAAAGAA GAAACACCAG AAAC             44

(2) INFORMATION FOR SEQ ID NO: 8:

(i) SEQUENCE CHARACTERISTICS:
        (A) LENGTH: 9 amino acids
        (B) TYPE: amino acid
        (C) STRANDEDNESS: <Unknown>
        (D) TOPOLOGY: linear (xi) SEQUENCE DESCRIPTION: SEQ ID NO: 8:

Val Glu Asn Lys Glu Glu Thr Pro Glu
1               5

(2) INFORMATION FOR SEQ ID NO: 9:

(i) SEQUENCE CHARACTERISTICS:
        (A) LENGTH: 47 base pairs
        (B) TYPE: nucleic acid
        (C) STRANDEDNESS: single
        (D) TOPOLOGY: linear (xi) SEQUENCE DESCRIPTION: SEQ ID NO: 9:

CAGCAGCAGG ATTCTTATTA TTCTTCTGGT TTTTCGTCAA CTTTCTT          47

(2) INFORMATION FOR SEQ ID NO: 10:

(i) SEQUENCE CHARACTERISTICS:
        (A) LENGTH: 44 base pairs
        (B) TYPE: nucleic acid
```

(C) STRANDEDNESS: single
            (D) TOPOLOGY: linear (xi) SEQUENCE DESCRIPTION: SEQ ID NO: 10:

CAGCAGCAGC CATGGGTTCT TCTGGTTTTT CGTCAACTTT CTTA                         44

(2) INFORMATION FOR SEQ ID NO: 11:

(i) SEQUENCE CHARACTERISTICS:
            (A) LENGTH: 34 base pairs
            (B) TYPE: nucleic acid
            (C) STRANDEDNESS: single
            (D) TOPOLOGY: linear (xi) SEQUENCE DESCRIPTION: SEQ ID NO: 11:

GGCCATGGAC ACTTACAAAT TAATCCTTAA TGGT                                    34

(2) INFORMATION FOR SEQ ID NO: 12:

(i) SEQUENCE CHARACTERISTICS:
            (A) LENGTH: 10 amino acids
            (B) TYPE: amino acid
            (C) STRANDEDNESS: <Unknown>
            (D) TOPOLOGY: linear (xi) SEQUENCE DESCRIPTION: SEQ ID NO: 12:

Met Asp Thr Tyr Lys Leu Ile Leu Asn Gly
1               5                   10

(2) INFORMATION FOR SEQ ID NO: 13:

(i) SEQUENCE CHARACTERISTICS:
            (A) LENGTH: 42 base pairs
            (B) TYPE: nucleic acid
            (C) STRANDEDNESS: single
            (D) TOPOLOGY: linear (xi) SEQUENCE DESCRIPTION: SEQ ID NO: 13:

CAGGTCGACT TATTACATTT CAGTTACCGT AAAGGTCTTA GT                           42

(2) INFORMATION FOR SEQ ID NO: 14:

(i) SEQUENCE CHARACTERISTICS:
            (A) LENGTH: 152 base pairs
            (B) TYPE: nucleic acid
            (C) STRANDEDNESS: single
            (D) TOPOLOGY: linear (xi) SEQUENCE DESCRIPTION: SEQ ID NO: 14:

AAGCTTAAGG AGGTTAATCG ATGAAAAAAA CTGCTATCGC TATCGCTGTT GCTCTGGCTG        60

GTTTCGCTAC TGTTGCTCAG GCGGCGCCGA GATCTAAACA GGAATTCGAG CTCGGTACC        120

GGGGATCCTC TAGAGCTGAC CTGCAGGCAT GC                                     152

(2) INFORMATION FOR SEQ ID NO: 15:

(i) SEQUENCE CHARACTERISTICS:
            (A) LENGTH: 4 amino acids
            (B) TYPE: amino acid
            (C) STRANDEDNESS: <Unknown>
            (D) TOPOLOGY: linear (xi) SEQUENCE DESCRIPTION: SEQ ID NO: 15:

Ala Val Glu Asn
1